United States Patent
Gschwend et al.

(10) Patent No.: US 8,148,378 B2
(45) Date of Patent: Apr. 3, 2012

(54) PYRIDAZINE DERIVATIVES AND THEIR USE AS INHIBITORS OF STEAROYL-CoA DESATURASE-1 ACTIVITY IN A MAMMAL

(75) Inventors: Heinz W. Gschwend, Santa Rosa, CA (US); Vishnumurthy Kodumuru, Waltham, MA (US); Shifeng Liu, Coquitlam (CA); Rajender Kamboj, Burnaby (CA)

(73) Assignee: Xenon Pharmaceuticals Inc., Burnaby, BC (CA)

( * ) Notice: Subject to any disclaimer, the term of this patent is extended or adjusted under 35 U.S.C. 154(b) by 176 days.

(21) Appl. No.: 12/390,117

(22) Filed: Feb. 20, 2009

(65) Prior Publication Data

US 2009/0197890 A1     Aug. 6, 2009

Related U.S. Application Data

(63) Continuation-in-part of application No. 10/566,856, filed as application No. PCT/US2004/024541 on Jul. 29, 2004, now Pat. No. 7,514,436.

(60) Provisional application No. 60/491,116, filed on Jul. 30, 2003, provisional application No. 60/491,095, filed on Jul. 30, 2003.

(51) Int. Cl.
  *A61K 31/501* (2006.01)
  *A61P 3/06* (2006.01)
  *A61P 9/00* (2006.01)
  *A61P 3/10* (2006.01)
  *A61P 3/04* (2006.01)
  *A61P 3/00* (2006.01)

(52) U.S. Cl. .................................. 514/252.02
(58) Field of Classification Search .................. 514/218, 514/252.02
See application file for complete search history.

(56) References Cited

U.S. PATENT DOCUMENTS

| | | | |
|---|---|---|---|
| 2,985,657 A | 5/1961 | Janssen | |
| 5,166,147 A | 11/1992 | Earl | |
| 7,196,080 B2 | 3/2007 | Iwata et al. | |
| 2005/0065143 A1* | 3/2005 | Chakka et al. | 514/218 |
| 2005/0119252 A1* | 6/2005 | Tucci et al. | 514/218 |
| 2006/0205713 A1* | 9/2006 | Gschwend et al. | 514/218 |
| 2009/0170836 A1* | 7/2009 | Angibaud et al. | 514/218 |

FOREIGN PATENT DOCUMENTS

| | | |
|---|---|---|
| EP | 0009655 A1 | 4/1980 |
| EP | 0 156 433 A | 10/1985 |
| EP | 0156433 | 10/1985 |
| EP | 0 211 457 A | 2/1987 |
| EP | 0 320 032 A | 6/1989 |
| EP | 0320032 A | 6/1989 |
| EP | 1 396 487 A | 3/2004 |
| EP | 1396487 A | 3/2004 |
| JP | 55-069577 A | 5/1980 |
| JP | 60-226862 A | 11/1985 |
| JP | 1207278 A | 8/1989 |
| JP | 10-007572 A | 1/1998 |
| JP | 2003-64057 A | 9/2004 |
| WO | 97/37975 | 10/1997 |
| WO | 99/00386 | 1/1999 |
| WO | 01/62954 | 8/2001 |
| WO | 02/10154 | 2/2002 |
| WO | 0210154 A2 | 2/2002 |
| WO | 02/102778 | 12/2002 |
| WO | 03/066604 A2 | 8/2003 |
| WO | 03/075929 | 9/2003 |
| WO | 03/076422 | 9/2003 |
| WO | 03/091247 A2 | 11/2003 |
| WO | 2004/052864 A1 | 6/2004 |

OTHER PUBLICATIONS

Dobrzyn, et al., Obesity Reviews 6, 169-174, 2005.*
Giutiérrez-Juárez, et al., J. Clin. Invest., vol. 116, No. 6, Jun. 2006, pp. 1686-1695.*
Sjogren, et al., Diabetologia (2008) 51:328-335.*
Ntambi, et al., PNAS, Aug. 20, 2002, vol. 99, #17, 11482-11486.*
Park, et al., J. Nutr. (1997), vol. 127, pp. 566-573.*
Miyazaki, et al. (I), J. Lipid Res., vol. 42, 2001, 1018-1024.*
Miyazaki, et al. (II), J. Nutrition, Jun. 23, 2001, 2260-2268.*
Attie, et al., J. Lipid Res., vol. 43, 2002, 1899-1907.*
Zheng, et al., Nat. Genet. (1999) 23:268-270.*
Warensjo, et al., Obesity, 15(7):1732-1740, Jul. 2007.*

(Continued)

*Primary Examiner* — James O Wilson
*Assistant Examiner* — Cecilia M Jaisle
(74) *Attorney, Agent, or Firm* — Seed IP Law Group PLLC

(57) ABSTRACT

A method of treating an SCD-mediated disease or condition in a mammal, preferably a human, includes administering to a mammal a compound of formula (I):

where x, y, W, V, $R^2$, $R^3$, $R^4$, $R^5$, $R^6$, $R^{6a}$, $R^7$, $R^{7a}$, $R^8$, $R^{8a}$, $R^9$ and $R^{9a}$ are defined herein. The SCD-mediated disease or condition may be selected from the group consisting of Type II diabetes, impaired glucose tolerance, insulin resistance, obesity, fatty liver, non-alcoholic steatohepatitis, dyslipidemia, metabolic syndrome, acne, cardiovascular disease, hypertriglyceridemia, inflammation, cancer, and any combination of these.

29 Claims, No Drawings

OTHER PUBLICATIONS

EPO Communication pursuant to Article 94(3) EPC (Office Action) issued Aug. 23, 2010, by the European Patent Office, in related European Patent Application No. EP-04779555.4 (4 pages).
Hori, T. et al.; "Studies on Antitumor-Active 2, 3-Dioxopiperazine Derivatives. III. Synthesis and Struct-Antitumor Activity Relationship of 1-(4-Aminobenzyl)-2, 3-dioxopiperazine Derivatives"; Chemical and Pharmaceutical Bulletin, Pharmaceutical Society of Japan, TOkyo, JP; vol. 29, No. 5, XP-001063113 (1981); pp. 1253-1266).
Steck, et al. "Pyridazines. VII. Some 3-Dialkylaminopyridazines (1)"; Sterling-Winthrop Research Institute, vol. 11 (1974); pp. 1077-1079.
Toldy, L. et al. "Piperazinderavate, I. 3, 4, 5-Trimethoxybenzoylderivate, Eine Neue Verbindungsgruppe Mit Antiulzerogener Wirkung"; Acta Chemica Academiae Scientiarum, Hungarica, Budapest, Hu., vol. 49, No. 3 (1966); pp. 265-286.
Ratouis, et al. "Synthesis and Pharmacological Study of New Piperazine Derivatives"; XP-002315168, vol. 8, Jan. 1965; pp. 104-107.
Database Caplus "Online! Chemical Abstracts Service, Columbus, Ohio, US; RN: 15567-65-4, 1967, Toldy, et. al., Piperazine Derivatives . . . " retrieved from STN Database accession No. AN: 1967:473577 abstract and Acta Chim. Acad.Sci.Hung., vol. 52, No. 3 (1967); pp. 283-299.
Database Caplus "Online! Chemical Abstracts Service, Columbus, Ohio, US; RN: 18524-49-7, 1968, Toldy, et. al., Phenothiazine derivatives . . . " retrieved from STN Database accession No. AN: 1968:95776 abstract and Acta Chim. Acad.Sci.Hung., vol. 53, No. 3 (1967); pp. 279-294.
International Search Report for related PCT/US2004/024541, published Feb. 10, 2005 (8 pages).
Office Action issued Jan. 27, 2009, by the Canadian Intellectual Property Office in related-Canadian Patent Application No. 2,533,897 (3 pages).
Hori, T., et al., "Studies on Antitumor-Active 2, 3-Dioxopiperazine Derivatives. III. Synthesis and Struct-Antitumor Activity Relationship of 1-(4-Aminobenzyl)-2, 3-dioxopiperazine Derivatives"; Chemical and Pharmaceutical Bulletin, Pharmaceutical Society of Japan, Tokyo, JP; vol. 29, No. 5, XP-001063113 (1981); pp. 1253-1266.
Steck, et al., "Pyridazines. VII. Some 3-Dialkylaminopyridazines (1)"; Sterling-Winthrop Research Institute, vol. 11 (1974); pp. 1077-1079.
Toldy, L., et al., "Piperazinderavate, 1. 3, 4, 5-Trimethoxybenzoylderivate, Eine Neue Verbindungsgruppe Mit Antiulzerogener Wirkung"; Acta Chemica Academiae Scientiarum, Hungarica, Budapest, Hu., vol. 49, No. 3 (1966); pp. 265-286.
Ratouis, et al., "Synthesis and Pharmacological Study of New Piperazine Derivatives"; XP-002315168, vol. 8, Jan. 1965; pp. 104-107.
Boissier, J. R., et al., "Synthesis and Pharmacological Study of New Piperazine Derivatives"; XP-001148182, vol. 6; pp. 541-544.
Official Action issued Oct. 19, 2010, by the Japan Patent Office in related Japanese Patent Application No. JP 2006-522072, with a partial English translation of the claims and Abstract. (9 pages).
Boissier, J. R., et al., "Synthesis and Pharmacological Study of New Piperazine Derivatives. I. Benzylpiperazines"; Journal of Medicinal Chemistry, American Chemical Sociaty, Washington, DC, U.S.; vol. 6, Sep. 1963; XP-001148182, ISSN: 0022-2623; pp. 541-544.
Regnier, et. al., "Triphenylpropylpiperazine Derivatives as New Potent Analgetic Substances"; Journal of Medicinal Chemistry (1972), vol. 15, No. 3; pp. 295-301.
EPO Extended European Search Report dated Mar. 29, 2011, from the European Patent Office in related European Patent Application No. EP-10184440.5 (11 pages).
Final Rejection (Office Action) issued Mar. 22, 2011, by the Japan Patent Office in related Japanese Patent Application No. JP2006-522072 (3 pages).
EPO Communication pursuant to Article 94(3) EPC (Office Action) issued Mar. 23, 2011, by the European Patent Office in related European Patent Application No. EP-04779555.4 (3 pages).
Cohen et al., "Role for Stearoyl-CoA Desaturase-1 in Leptin-Mediated Weight Loss," *Science* 297: 240-243, Jul. 12, 2002.
de Antueno et al., "Relationship Between Mouse Liver Δ9 Desaturase Activity and Plasma Lipids," *Lipids* 28(4): 285-290, 1993.
Jeffcoat and James, *New Comprehensive Biochemistry Volume 7: Fatty Acid Metabolism and Its Regulation*, Elsevier Science Publishers B.V., Amsterdam, The Netherlands, Chapter 4, "The regulation of desaturation and elongation of fatty acids in mammals," 85-112, 1984.

\* cited by examiner

PYRIDAZINE DERIVATIVES AND THEIR USE AS INHIBITORS OF STEAROYL-COA DESATURASE-1 ACTIVITY IN A MAMMAL

CROSS-REFERENCE TO RELATED APPLICATIONS

This is a Continuation-In-Part (CIP) application and claims benefit under 35 U.S.C. §120 of U.S. patent application Ser. No. 10/566,856, filed Jan. 30, 2006, which is a national phase application based on PCT/US2004/024541, filed Jul. 29, 2004, which claims the benefit of U.S. Provisional Patent Application Ser. No. 60/491,116, filed Jul. 30, 2003 and U.S. Provisional Patent Application Ser. No. 60/491,095, filed Jul. 30, 2003. These prior applications are hereby incorporated by reference in their entireties.

FIELD OF THE INVENTION

The present invention relates generally to the field of inhibitors of stearoyl-CoA desaturase, such as pyridazine derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome and the like.

BACKGROUND OF THE INVENTION

Acyl desaturase enzymes catalyze the formation of double bonds in fatty acids derived from either dietary sources or de novo synthesis in the liver. Mammals synthesize at least three fatty acid desaturases of differing chain length specificity that catalyze the addition of double bonds at the delta-9, delta-6, and delta-5 positions. Stearoyl-CoA desaturases (SCDs) introduce a double bond in the C9-C10 position of saturated fatty acids. The preferred substrates are palmitoyl-CoA (16:0) and stearoyl-CoA (18:0), which are converted to palmitoleoyl-CoA (16:1) and oleoyl-CoA (18:1), respectively. The resulting mono-unsaturated fatty acids are substrates for incorporation into phospholipids, triglycerides, and cholesteryl esters.

A number of mammalian SCD genes have been cloned. For example, two genes have been cloned from rat (SCD1, SCD2) and four SCD genes have been isolated from mouse (SCD1, 2, 3, and 4). A single SCD gene, SCD1, has been characterized in humans. SCD1 is described in Brownlie et al, PCT published patent application, WO 01/62954, the disclosure of which is hereby incorporated by reference in its entirety. A second human SCD isoform has recently been identified, and because it bears little sequence homology to alternate mouse or rat isoforms it has been named human SCD5 or hSCD5 (PCT published patent application, WO 02/26944, incorporated herein by reference in its entirety).

The biochemical roles of SCD have been known in rats and mice since the 1970's (Jeffcoat, R. et al., *Elsevier Science* (1984), Vol. 4, pp. 85-112; de Antueno, R J, *Lipids* (1993), Vol. 28, No. 4, pp. 285-290). More recently, it has also been directly implicated in various human disease processes, including type II diabetes, insulin resistance, obesity, dyslipidemia, hypertriglyceridemia, acne, inflammation, metabolic syndromes, and cancer.

Patients with type II diabetes produce insulin, but lose the ability to respond to insulin, i.e., the patients have decreased insulin sensitivity. Ntambi, J. M. et al., *Proc. Natl. Acad. Sca*, (Aug. 20, 2002), Vol. 99, No. 17, pp. 11482-6, shows that mice with disrupted SCD-1 activity have increased insulin sensitivity (first paragraph, p. 11482). It further shows that SCD-1 knock-out mice exhibit improved glucose tolerance and a greater response to glucose lowering effects of insulin, when compared with the wild-type mice (p. 11484). These results suggest that inhibition of stearoyl-CoA desaturase-1 activity can increase insulin sensitivity, thereby preventing or treating Type II diabetes.

In a study by Sjogren, P. et al., *Diabetologia*, (2008), 51(2): 328-35, involving 294 men, it was shown that elevated SCD activity within adipose tissue is closely coupled to the development of insulin resistance. In addition, Warensjo, E. et al., *Obesity*, (2007), 15(7):1732-40, shows that, in a study involving 1143 men, genetic variations, e.g., single nucleotide polymorphisms, in the SCD-1 gene are associated with insulin sensitivity. Together, the data obtained from animal and human studies support the idea that elevated SCD activity is linked to insulin resistance and inhibition of SCD-1 activity may lead to increased insulin sensitivity. Therefore, the SCD-1 inhibitor compounds may be used in treating/preventing animals or humans for type II diabetes and/or for increasing insulin sensitivity.

Park, E. I. et al., *J. Nutr.* (1997), Vol. 127, pp. 566-573, show that mice provided with a diet that lowered the expression of SCD-1 had lower body weights and lower serum concentrations of total cholesterol, triglycerides and HDL cholesterol. Furthermore, Ntambi et al, cited above, showed that loss of SCD-1 function (activity) protects mice from gaining weight from a high-fat diet. Importantly, Hulver, et al., *Cell Metabolism*, (2005), 2:251-61, shows that SCD-1 is robustly up-regulated in skeletal muscle from extremely obese people. Thus, SCD-1 inhibitors may be used to treat obesity.

In addition, SCD-1 inhibitors may be used to treat dyslipidemia and hypertriglyceridemia by lowering triglyceride, LDL and VLDL serum levels. WO 01/62954 discloses an animal model for testing the claimed compounds' effectiveness in lowering triglyceride, LDL and VLDL serum levels (see Example 1) and demonstrates the correlation between SCD-1 activity in humans and the levels of serum triglycerides (see Example 2). Consistently, as noted by Miyazaki, M. et al., *Journal of Lipid Research* (2001), Vol. 42, pp. 1018-1024, triglyceride synthesis can be dramatically reduced in the liver of SCD-1 knock-out mice fed a lipogenic diet, as compared with the normal mice. See also, Miyazaki, M. et al., *J. Biol. Chem.* (2000), Vol. 275, No. 39, pp. 30132-30138. Furthermore, Attie, A. D. et al., *Journal of Lipid Research* (2002), Vol. 43, pp. 1899-1907, shows that SCD activity may be rate-limiting in triglyceride production in a wide array of dyslipidemias. Savransky, et al., *Cir. Res.*, (2008), 103:1173-80, also shows that down-regulation of SCD-1 gene by anti-sense oligonucleotides can attenuate the chronic intermittent hypoxia-induced dyslipidemia and atherosclerosis in mice. In humans, Savransky, et al., *Cir. Res.*, (2008), 103:1173, further shows that the expression levels of SCD gene are correlated well with dyslipidemia in patients exhibiting chronic intermittent hypoxia. These observations demonstrate that the induction of triglyceride synthesis is highly dependent upon the expression of the SCD-1 gene. Therefore, the SCD-1 inhibitor compounds may be useful in treating hypertriglyceridemia by lowering triglyceride, LDL, and VLDL serum levels and in treating dyslipidemia in a human subject.

SCD-1 inhibitor compounds may be used to treat metabolic syndrome. The term "metabolic syndrome" is a recognized clinical term. Metabolic syndrome is a combination of medical disorders that increase the risk of developing cardiovascular disease and diabetes, and may be used to describe a condition comprising at least one of type II diabetes, impaired glucose tolerance and insulin resistance, together with one or more symptoms of hypertension, obesity, hypertriglyceridemia, low HDL and microalbuminemia. In other words, the term "metabolic syndrome" may be used to describe a cluster of metabolic abnormalities. Thus, disorders like dyslipidemia, hypertension and obesity may be components of the metabolic syndrome and inhibition of SCD-1 activity can be a therapeutic treatment for each of these disorders individually or collectively. Given that SCD-1 is a key regulator of fatty acid metabolism and insulin action (see Ntambi, J. M. et al., *Journal of Lipid Research* (1999), Vol. 40, pp. 1549-1558), a compound that inhibits SCD-1 activity can impact more than one component of the metabolic syndrome and may be useful in treating this disease.

SCD-1 inhibitors may also be used to treat acne. Zheng et al., *Nat. Genet.* (1999) 23:268-270, show that rodents lacking a functional SCD-1 gene have changes to the condition of their eyes, skin and coat thereby reducing the excessive sebum production that typically results in the formation of acne. As noted by Miyazaki et al., J. Nutr. (2001), Vol. 131, pp 2260-68, SCD-1 knock-out mice developed cutaneous abnormalities and atrophic sebaceous and meibomian glands compared to normal mice. Modulation of SCD activity can be of importance in the treatment of disease states that are associated with changes in the lipid composition in the sebaceous and meibomian glands and their lipid secretions as well as changes in the composition of circulating lipids that impact these tissues (see Ntambi J et al., *J. Lipid Res*. (1999), (40): 1549) and US Patent Publication No. 2005/0151018). These observations demonstrate that reduction of the sebum production can be effected by the inhibition of SCD-1. Therefore, by virtue of their ability to inhibit SCD-1 activity, SCD-1 inhibitors may be useful in treating acne in humans.

In a large population-based cohort study involved 767 men, Petersson, H., et al., *Br. J. Nutr.* (2008), 99(6):1186-9, shows that inflammation, as indicated by an increased concentration of serum C-reactive protein (CRP), is positively associated with SCD-1 activity. The same group of investigators further confirms their previous observation by showing that SCD-1 index is positively correlated with CRP, and thus inflammation, in 264 older men and women aged 70 (Petersson, H., et al., *Atherosclerosis*. (2008), July 1, Epub ahead of print). Therefore, SCD-1 inhibitors may be used to treat inflammation.

SCD-1 inhibitors may also be used to treat cancer. Saturated (SFA) and monounsaturated fatty acids (MUFA), the most abundant fatty acid species, are involved in the regulation of various cellular functions, including proliferation, programmed cell death (or apoptosis), and lipid-mediated cytotoxicity. High levels of MUFA have been associated with several types of cancers. Because SCD regulates the conversion of SFA into MUFA, SCD may be involved in tumorigenbesis. Indeed, increased expression of SCD gene has been found in colonic and esophageal carcinoma, and in hepatocellular adenoma (Li, J. et al., *Int. J. Cancer*, (1994), 57:348-52); and in chemically induced tumors (That, S. F., et al., *Carcinogenesis* (2001), 22:1317-22). Consistently, both SCD gene expression and fatty acid synthesis are found higher in the transformed human lung fibroblasts than that of their normal counterparts (Scaglia, N. et al., *Biochim. Biophys. Acta*, (2005), 1687:141-51). Scaglia, N. et al., *J. Biol. Chem.*, (2005), 280:25339-49, and Scaglia, N. et al., *Int. J. Oncol*., (2008), 33:839-50, further shows that down-regulation of SCD-1 gene, using antisense approach, in the transformed human lung fibroblasts or in a human lung adenocarcinoma cell line (A549) reverses two hall-marks of neoplastic transformation, i.e., proliferation and anchorage-independent growth. In addition, increased apoptosis and deactivation of cancer-related genes, e.g., AKT and GSK3β, are found in the SCD-1 down-regulated A549 cells. Importantly, the reduction of SCD-1 gene expression in human lung cancer cells significantly delays the formation of tumors and reduces the growth rate of tumor xenografts in mice. These data demonstrate the anti-tumor activity of agents that can reduce SCD-1 expression and/or inhibit SCD-1 activity in human cancer cells. Therefore, by virtue of their ability to inhibit SCD-1 activity, SCD-1 inhibitors may be useful in treating cancer in humans.

The present invention presents new classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

Related Literature

PCT Published Patent Applications, WO 03/075929, WO 03/076400 and WO 03/076401 disclose compounds having histone deacetylase inhibiting enzymatic activity.

BRIEF SUMMARY OF THE INVENTION

The present invention provides pyridazine derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides methods of inhibiting human stearoyl-CoA desaturase (hSCD) activity comprising contacting a source of hSCD with a compound of formula (I):

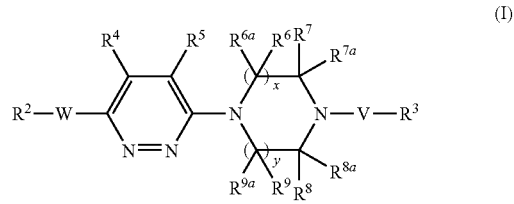

wherein:
x and y are each independently 1, 2 or 3;
W is —O—, —C(O)O—, —N($R^1$)—, —S(O)$_t$— (where t is 0, 1 or 2), —N($R^1$)S(O)$_2$—, —OC(O)— or —C(O)—;
V is —C(O)—, —C(S)—, —C(O)N($R^1$)—, —C(O)O—, —S(O)$_2$—, —S(O)$_2$N($R^1$)— or —C($R^1$)H—;
each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or —$N(R^{13})_2$;

$R^6$, $R^{6a}$, $R^7$, $R^{7a}$, $R^8$, $R^{8a}$, $R^9$ and $R^{9a}$ are each independently selected from hydrogen or $C_1$-$C_3$alkyl;

or $R^7$ and $R^{7a}$ together, or $R^8$ and $R^{8a}$ together, or $R^9$ and $R^{9a}$ together, or $R^6$ and $R^{6a}$ together are an oxo group, provided that when V is —C(O)—, $R^7$ and $R^{7a}$ together or $R^8$ and $R^{8a}$ together do not form an oxo group, while the remaining $R^7$, $R^{7a}$, $R^8$, $R^{8a}$, $R^9$, $R^{9a}$, $R^6$ and $R^{6a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

$R^{11}$ is hydrogen or $C_1$-$C_3$alkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, this invention provides methods of treating a disease or condition mediated by stearoyl-CoA desaturase (SCD) in a mammal, wherein the method comprises administering to the mammal in need thereof a therapeutically effective amount of a compound of formula (I) as set forth above.

In another aspect, this invention provides compounds of formula (I) having the following formula (Ia)

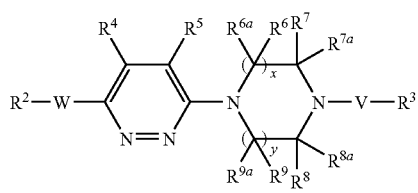

(Ia)

wherein:

x and y are each independently 1, 2 or 3;

W is —O—, —C(O)O—, —$N(R^1)$—, —$S(O)_t$— (where t is 0, 1 or 2), —$N(R^1)S(O)_2$—, —OC(O)— or —C(O)—;

V is —C(O)—, —C(S)—, —$C(O)N(R^1)$—, —C(O)O—, —$S(O)_2$—, —$S(O)_2N(R^1)$— or —$C(R^{11})H$—;

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl, provided that, when W is —C(O)—, $R^2$ can not be $C_1$-$C_6$alkyl substituted by —$S(O)_tR^{14}$ where $R^{14}$ is hydrogen, $C_1$-$C_6$alkyl, $C_7$-$C_{12}$aralkyl, pyrazinyl, pyridinonyl, pyrrolidionyl or imidazolyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or —$N(R^{13})_2$;

$R^6$, $R^{6a}$, $R^7$, $R^{7a}$, $R^8$, $R^{8a}$, $R^9$ and $R^{9a}$ are each independently selected from hydrogen or $C_1$-$C_3$alkyl;

or $R^7$ and $R^{7a}$ together, or $R^8$ and $R^{8a}$ together, or $R^9$ and $R^{9a}$ together, or $R^6$ and $R^{6a}$ together are an oxo group, provided that when V is —C(O)—, $R^7$ and $R^{7a}$ together or $R^8$ and $R^{8a}$ together do not form an oxo group, while the remaining $R^7$, $R^{7a}$, $R^8$, $R^{8a}$, $R^9$, $R^{9a}$, $R^6$ and $R^{6a}$ are each independently selected from hydrogen or $C_1$-$C_3$alkyl;

or one of $R^6$, $R^{6a}$, $R^7$, and $R^{7a}$ together with one of $R^8$, $R^{8a}$, $R^9$ and $R^{9a}$ form an alkylene bridge, while the remaining $R^6$, $R^{6a}$, $R^7$, $R^{7a}$, $R^8$, $R^{8a}$, $R^9$, and $R^{9a}$ are each independently selected from hydrogen or $C_1$-$C_3$alkyl;

$R^{11}$ is hydrogen or $C_1$-$C_3$alkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

DETAILED DESCRIPTION OF THE INVENTION

Definitions

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Methoxy" refers to the —$OCH_3$ radical.
"Cyano" refers to the —CN radical.
"Nitro" refers to the —$NO_2$ radical.
"Trifluoromethyl" refers to the —$CF_3$ radical.
"Oxo" refers to the =O substituent.
"Thioxo" refers to the =S substituent.
"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, —$OR^{14}$, —OC(O)—$R^{14}$, —$N(R^4)_2$, —C(O)$R^{14}$, —C(O)O$R^{14}$, —C(O)N($R^{14}$)$_2$, —N($R^{14}$)C(O)O$R^{16}$, —N($R^{14}$)C(O)$R^{16}$, —N($R^{14}$)(S(O)$_t$$R^{16}$) (where t is 1 to 2), —S(O)O$R^{16}$ (where t is 1 to 2), —S(O)$_t$$R^{16}$ (where t is 0 to 2), and —S(O)$_t$N($R^{14}$)$_2$ (where t is 1 to 2) where each $R^{14}$ is independently hydrogen, alkyl, haloalkyl, cycloalkyl, cycloalkylalkyl, aryl (optionally substituted with one or more halo groups), aralkyl, heterocyclyl, heterocylylalkyl, heteroaryl or heteroarylalkyl; and each $R^{16}$ is alkyl, haloalkyl, cycloalkyl, cycloalkylalkyl, aryl, aralkyl, heterocyclyl, heterocylylalkyl, heteroaryl or heteroarylalkyl, and where each of the above substituents is unsubstituted unless otherwise indicated.

"$C_1$-$C_3$alkyl" refers to an alkyl radical as defined above containing one to three carbon atoms. The $C_1$-$C_3$alkyl radical may be optionally substituted as defined for an alkyl group.

"$C_1$-$C_6$alkyl" refers to an alkyl radical as defined above containing one to six carbon atoms. The $C_1$-$C_6$alkyl radical may be optionally substituted as defined for an alkyl group.

"$C_1$-$C_{12}$alkyl" refers to an alkyl radical as defined above containing one to twelve carbon atoms. The $C_1$-$C_{12}$alkyl radical may be optionally substituted as defined for an alkyl group.

"$C_2$-$C_6$alkyl" refers to an alkyl radical as defined above containing two to six carbon atoms. The $C_2$-$C_6$alkyl radical may be optionally substituted as defined for an alkyl group.

"$C_3$-$C_6$alkyl" refers to an alkyl radical as defined above containing three to six carbon atoms. The $C_3$-$C_6$alkyl radical may be optionally substituted as defined for an alkyl group.

"$C_3$-$C_{12}$alkyl" refers to an alkyl radical as defined above containing three to twelve carbon atoms. The $C_3$-$C_{12}$alkyl radical may be optionally substituted as defined for an alkyl group.

"$C_6$-$C_{12}$alkyl" refers to an alkyl radical as defined above containing six to twelve carbon atoms. The $C_6$-$C_{12}$alkyl radical may be optionally substituted as defined for an alkyl group.

"$C_7$-$C_{12}$alkyl" refers to an alkyl radical as defined above containing seven to twelve carbon atoms. The $C_7$-$C_{12}$alkyl radical may be optionally substituted as defined for an alkyl group.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$OR^4$, —OC(O)—$R^{14}$, —$N(R^4)_2$, —C(O)$R^4$, —C(O)O$R^4$, —C(O)N($R^{14}$)$_{27}$—N ($R^{14}$)C(O)O$R^{16}$, —N($R^{14}$)C(O)$R^{16}$, —N($R^{14}$)(S(O)$_t$$R^{16}$) (where t is 1 to 2), —S(O)$_t$O$R^{16}$ (where t is 1 to 2), —S(O)$_t$$R^{16}$ (where t is 0 to 2), and —S(O)$_t$N($R^{14}$)$_2$ (where t is 1 to 2) where each $R^{14}$ is independently hydrogen, alkyl, haloalkyl, cycloalkyl, cycloalkylalkyl, aryl, aralkyl, heterocyclyl, heterocylylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$alkenyl" refers to an alkenyl radical as defined above containing three to 12 carbon atoms. The $C_3$-$C_{12}$alkenyl radical may be optionally substituted as defined for an alkenyl group.

"$C_2$-$C_{12}$alkenyl" refers to an alkenyl radical as defined above containing two to 12 carbon atoms. The $C_2$-$C_{12}$alkenyl radical may be optionally substituted as defined above for an alkenyl group.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkylene bridge" refers to a straight or branched divalent hydrocarbon bridge, linking two different carbons of the same ring structure, consisting solely of carbon and hydrogen, containing no unsaturation and having from one to twelve carbon atoms, preferably having from one to eight carbons, e.g., methylene, ethylene, propylene, n-butylene, and the like. The alkylene bridge may link any two carbons within the ring structure.

"Alkoxy" refers to a radical of the formula —$OR_a$ where $R_a$ is an alkyl radical as defined above. The alkyl part of the alkoxy radical may be optionally substituted as defined above for an alkyl radical.

"$C_1$-$C_6$alkoxy" refers to an alkoxy radical as defined above containing one to six carbon atoms. The alkyl part of the $C_1$-$C_6$alkoxy radical may be optionally substituted as defined above for an alkyl group.

"$C_1$-$C_{12}$alkoxy" refers to an alkoxy radical as defined above containing one to twelve carbon atoms. The alkyl part of the $C_1$-$C_{12}$alkoxy radical may be optionally substituted as defined above for an alkyl group.

"$C_3$-$C_{12}$alkoxy" refers to an alkoxy radical as defined above containing three to twelve carbon atoms. The alkyl part of the $C_3$-$C_{12}$alkoxy radical may be optionally substituted as defined above for an alkyl group.

"Alkoxyalkyl" refers to a radical of the formula —$R_a$—O—$R_a$ where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"$C_2$-$C_{12}$alkoxyalkyl" refers to an alkoxyalkyl radical as defined above containing two to twelve carbon atoms. Each alkyl part of the $C_2$-$C_{12}$alkoxyalkyl radical may be optionally substituted as defined above for an alkyl group.

"$C_3$alkoxyalkyl" refers to an alkoxyalkyl radical as defined above containing three carbon atoms. Each alkyl part of the $C_3$alkoxyalkyl radical may be optionally substituted as defined above for an alkyl group.

"$C_3$-$C_{12}$alkoxyalkyl" refers to an alkoxyalkyl radical as defined above containing three to twelve carbon atoms. Each alkyl part of the $C_3$-$C_{12}$alkoxyalkyl radical may be optionally substituted as defined above for an alkyl group.

"Alkylsulfonyl" refers to a radical of the formula —$S(O)_2$$R_a$ where $R_a$ is an alkyl group as defined above. The alkyl part of the alkylsulfonyl radical may be optionally substituted as defined above for an alkyl group.

"$C_1$-$C_6$alkylsulfonyl" refers to an alkylsulfonyl radical as defined above having one to six carbon atoms. The $C_1$-$C_6$alkylsulfonyl group may be optionally substituted as defined above for an alkylsulfonyl group.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}OC(O)$—$R^{14}$, —$R^{15}$—$N(R^{14})_2$, —$R^5$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"$C_7$-$C_{12}$aralkyl" refers to an aralkyl group as defined above containing seven to twelve carbon atoms. The aryl part of the $C_7$-$C_{12}$aralkyl radical may be optionally substituted as described above for an aryl group. The alkyl part of the $C_7$-$C_{12}$aralkyl radical may be optionally substituted as defined above for an alkyl group.

"$C_7$-$C_{19}$aralkyl" refers to an aralkyl group as defined above containing seven to nineteen carbon atoms. The aryl part of the $C_7$-$C_{12}$aralkyl radical may be optionally substituted as described above for an aryl group. The alkyl part of the $C_7$-$C_{12}$aralkyl radical may be optionally substituted as defined above for an alkyl group.

"$C_{13}$-$C_{19}$aralkyl" refers to an aralkyl group as defined above containing thirteen to nineteen carbon atoms. The aryl part of the $C_{13}$-$C_{19}$aralkyl radical may be optionally substituted as described above for an aryl group. The alkyl part of the $C_{13}$-$C_{19}$aralkyl radical may be optionally substituted as defined above for an alkyl group.

"Aralkenyl" refers to a radical of the formula —$R_cR_b$ where $R_c$ is an alkenyl radical as defined above and $R_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aryloxy" refers to a radical of the formula —$OR_b$ where $R_b$ is an aryl group as defined above. The aryl part of the aryloxy radical may be optionally substituted as defined above.

"Aryl-$C_1$-$C_6$alkyl" refers to a radical of the formula —$R_h$—$R_i$ where $R_h$ is an unbranched alkyl radical having one to six carbons and $R_i$ is an aryl group attached to the terminal carbon of the alkyl radical.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, $R^{15}$—$N(R^{14})_2$, —$R^{15}$—$C(O)R^{14}$, $R^{15}$—$OC(O)R^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_6$cycloalkyl" refers to a cycloalkyl radical as defined above having three to six carbon atoms. The $C_3$-$C_6$cycloalkyl radical may be optionally substituted as defined above for a cycloalkyl group.

"$C_3$-$C_{12}$cycloalkyl" refers to a cycloalkyl radical as defined above having three to twelve carbon atoms. The $C_3$-$C_{12}$cycloalkyl radical may be optionally substituted as defined above for a cycloalkyl group.

"Cycloalkylalkyl" refers to a radical of the formula —$R_aR_d$ where $R_a$ is an alkyl radical as defined above and $R_d$ is a cycloalkyl radical as defined above. The cycloalkyl part of the cycloalkyl radical may be optionally substituted as defined above for an cycloalkyl radical. The alkyl part of the cycloalkyl radical may be optionally substituted as defined above for an alkyl radical.

"$C_4$-$C_{12}$cycloalkylalkyl" refers to a cycloalkylalkyl radical as defined above having four to twelve carbon atoms. The $C_4$-$C_{12}$cycloalkylalkyl radical may be optionally substituted as defined above for a cycloalkylalkyl group.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above, e.g., 2-bromoethenyl, 3-bromoprop-1-enyl, and the like. The alkenyl part of the haloalkenyl radical may be optionally substituted as defined above for an alkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{15}$, —$R^{15}$—$N(R^{14})C(O)R^{16}$, —$R^{15}$—$N(R^{14})(S(O)R^{16})$ (where t is 1 to 2), —$R^{15}$—$S(O)_tOR^{16}$ (where t is 1 to 2), —$R^{15}$—$S(O)_tR^{16}$ (where t is 0 to 2), and —$R^{15}$—$S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_3$-$C_{12}$heterocyclyl" refers to a heterocyclyl radical as defined above having three to twelve carbons. The $C_3$-$C_{12}$heterocyclyl may be optionally substituted as defined above for a heterocyclyl group.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"$C_3$-$C_{12}$heterocyclylalkyl" refers to a heterocyclylalkyl radical as defined above having three to twelve carbons. The $C_3$-$C_{12}$heterocyclylalkyl radical may be optionally substituted as defined above for a heterocyclylalkyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]

imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—OC(O)—$R^{14}$, —$R^{15}$—N($R^4$)$_2$, —$R^{15}$—C(O) $R^{14}$—$R^{15}$—C(O)O$R^{14}$, —$R^{15}$—C(O)N($R^{14}$)$_2$, —$R^{15}$—N ($R^{14}$)C(O)O$R^{16}$, —$R^{15}$—N($R^{14}$)C(O)$R^{16}$, —$R^{15}$—N($R^{14}$) (S(O)$_t$$R^{16}$) (where t is 1 to 2), —$R^{15}$—S(O)$_t$O$R^{16}$ (where t is 1 to 2), —$R^{15}$—S(O)$_t$$R^{16}$ (where t is 0 to 2), and —$R^{15}$—S (O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"$C_1$-$C_{12}$heteroaryl" refers to a heteroaryl radical as defined above having one to twelve carbon atoms. The $C_1$-$C_{12}$heteroaryl group may be optionally substituted as defined above for a heteroaryl group.

"$C_5$-$C_{12}$heteroaryl" refers to a heteroaryl radical as defined above having five to twelve carbon atoms. The $C_5$-$C_{12}$heteroaryl group may be optionally substituted as defined above for a heteroaryl group.

"Heteroarylalkyl" refers to a radical of the formula —$R_aR_f$— where $R_a$ is an alkyl radical as defined above and $R_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"$C_3$-$C_{12}$heteroarylalkyl" refers to a heteroarylalkyl radical as defined above having three to twelve carbon atoms. The $C_3$-$C_{12}$heteroarylalkyl group may be optionally substituted as defined above for a heteroarylalkyl group.

"Heteroarylcycloalkyl" refers to a radical of the formula —$R_dR_f$— where $R_d$ is a cycloalkyl radical as defined above and $R_f$ is a heteroaryl radical as defined above. The cycloalkyl part of the heteroarylcycloalkyl radical may be optionally substituted as defined above for a cycloalkyl group. The heteroaryl part of the heteroarylcycloalkyl radical may be optionally substituted as defined above for a heteroaryl group.

"Heteroarylalkenyl" refers to a radical of the formula —$R_bR_f$— where $R_b$ is an alkenyl radical as defined above and $R_f$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"$C_2$-$C_{12}$hydroxyalkyl" refers to a hydroxyalkyl radical as defined above containing two to twelve carbon atoms. The alkyl part of the $C_2$-$C_{12}$hydroxyalkyl radical may be optionally substituted as defined above for an alkyl group.

"$C_3$-$C_{12}$hydroxyalkyl" refers to a hydroxyalkyl radical as defined above containing three to twelve carbon atoms. The alkyl part of the $C_3$-$C_{12}$hydroxyalkyl radical may be optionally substituted as defined above for an alkyl group.

"$C_7$-$C_{12}$hydroxyalkyl" refers to a hydroxyalkyl radical as defined above containing seven to twelve carbon atoms. The alkyl part of the $C_7$-$C_{12}$hydroxyalkyl radical may be optionally substituted as defined above for an alkyl group.

"Hydroxyalkenyl" refers to a radical of the formula $R_c$—OH where $R_c$ is an alkenyl radical as defined above. The hydroxy group may be attached to the alkenyl radical on any carbon within the alkenyl radical. The alkenyl part of the hydroxyalkenyl group may be optionally substituted as defined above for an alkenyl group.

"$C_2$-$C_{12}$hydroxyalkenyl" refers to a hydroxyalkenyl radical as defined above containing two to twelve carbon atoms. The alkenyl part of the $C_2$-$C_{12}$hydroxyalkenyl radical may be optionally substituted as defined above for an alkenyl group.

"$C_3$-$C_{12}$hydroxyalkenyl" refers to a hydroxyalkenyl radical as defined above containing three to twelve carbon atoms. The alkenyl part of the $C_3$-$C_{12}$hydroxyalkenyl radical may be optionally substituted as defined above for an alkenyl group.

"Hydroxyl-$C_1$-$C_6$-alkyl" refers to a radical of the formula —$R_h$—OH where $R_h$ is an unbranched alkyl radical having one to six carbons and the hydroxy radical is attached to the terminal carbon.

"Trihaloalkyl" refers to an alkyl radical, as defined above, that is substituted by three halo radicals, as defined above, e.g., trifluoromethyl. The alkyl part of the trihaloalkyl radical may be optionally substituted as defined above for an alkyl group.

"$C_1$-$C_6$trihaloalkyl" refers to a trihaloalkyl radical as defined above having one to six carbon atoms. The $C_1$-$C_6$trihaloalkyl may be optionally substituted as defined above for a trihaloalkyl group.

"Trihaloalkoxy" refers to a radical of the formula —$OR_g$ where $R_g$ is a trihaloalkyl group as defined above. The trihaloalkyl part of the trihaloalkoxy group may be optionally substituted as defined above for a trihaloalkyl group.

"$C_1$-$C_6$trihaloalkoxy" refers to a trihaloalkoxy radical as defined above having one to six carbon atoms. The $C_1$-$C_6$trihaloalkoxy group may be optionally substituted as defined above for a trihaloalkoxy group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to other through direct bonds or some or all of the rings may be fused to each other. Examples include, but are not limited to a cycloalkyl radical substituted by aryl group; a cycloalkyl group substituted by an aryl group, which, in turn, is substituted by another aryl group; and so forth.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-oluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting or delaying its development;

(iii) relieving the disease or condition, i.e., causing regression of the disease or condition; or (iv) reducing the risk of developing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein employ and rely the chemical naming features as utilized by Chemdraw version 7.0.1 (available from Cambridgesoft Corp., Cambridge, Mass.). For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms which are assumed to be bonded to sufficient hydrogen atoms to complete the valency.

For example, a compound of formula (I), as set forth above in the Summary of the Invention, wherein x and y are each 1; W is —N($R^1$)—; V is —C(O)—; $R^1$ is methyl, $R^4$ and $R^5$ are each hydrogen; $R^6$, $R^{6a}$, $R^7$, $R^{7a}$, $R^8$, $R^{8a}$, $R^9$ and $R^{9a}$ are each hydrogen; $R^2$ is 2-phenylethyl (phenethyl); $R^3$ is 2-trifluoromethylphenyl; i.e., a compound of the following formula:

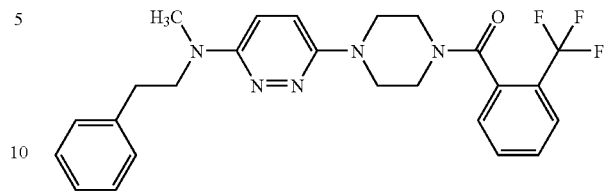

is named herein as {4-[6-(Methyl-phenethyl-amino)-pyridazin-3-yl]-piperazin-1-yl}-(2-trifluoromethyl-phenyl)-methanone.

Certain radical groups of the compounds of the invention are depicted herein as linkages between two parts of the compounds of the invention. For example, in the following formula (I):

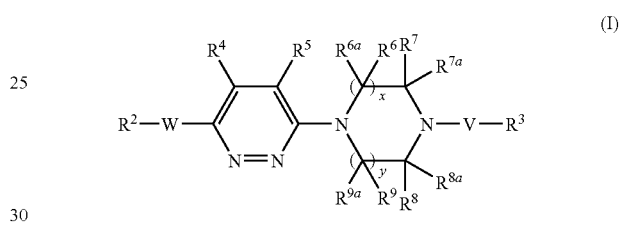

W is described, for example, as being —N($R^1$)S(O)$_2$—; and V is described, for example, as being —C(O)N($R^1$)—. This description is meant to describe a W group attached to the $R^2$ group as follows: $R^2$—N($R^1$)S(O)$_2$—; and meant to describe a V group attached to the $R^3$ group as follows: —C(O)N($R^1$)—$R^3$. In other words, the description of the W and V linkage groups are meant to be read from left to right in view of formula (I) as depicted above.

Embodiments of the Invention

In one embodiment of the invention, compounds of formula (Ia), as set forth above in the Summary of the Invention, are directed to compounds wherein x and y are each 1; W is —O—; V is —C(O)— or —C(S)—; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^4$ and $R^5$ are each hydrogen; and $R^6$, $R^{6a}$, $R^7$, $R^{7a}$, $R^8$, $R^{8a}$, $R^9$ and $R^{9a}$ are each hydrogen.

One embodiment of this embodiment are compounds wherein V is —C(O)—; $R^2$ is $C_7$-$C_{12}$aralkyl optionally substituted by one or more substituents selected from halo, cyano, nitro, hydroxy, $C_1$-$C_6$alkyl, $C_1$-$C_6$trihaloalkyl and $C_1$-$C_6$trihaloalkoxy; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^2$ is $C_7$-$C_{12}$aralkyl optionally substituted by one or more substituents selected from halo, $C_1$-$C_6$alkyl, $C_1$-$C_6$trihaloalkyl and $C_1$-$C_6$trihaloalkoxy; and $R^3$ is phenyl optionally substituted by one or more substituents selected from the group consisting of halo, $C_1$-$C_6$trihaloalkyl and $C_1$-$C_6$trihaloalkoxy.

Another embodiment of this embodiment are compounds wherein V is —C(O)—; $R^2$ is $C_1$-$C_{12}$alkyl or $C_2$-$C_{12}$alkenyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

Another embodiment of this embodiment are compounds wherein V is —C(O)—; $R^2$ is $C_3$-$C_{12}$cycloalkyl or $C_4$-$C_{12}$cycloalkylalkyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^2$ is $C_4$-$C_{12}$cycloalkylalkyl; and $R^3$ is phenyl optionally substituted by one or more substituents selected from the group consisting of halo, $C_1$-$C_6$trihaloalkyl and $C_1$-$C_6$trihaloalkoxy.

In another embodiment of the invention, compounds of formula (Ia), as set forth above in the Summary of the Invention, are directed to compounds wherein x and y are each 1; W is —S(O)$_t$— (where t is 0, 1 or 2); V is —C(O)— or —C(S)—; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^4$ and $R^5$ are each hydrogen; and $R^6$, $R^{6a}$, $R^7$, $R^{7a}$, $R^8$, $R^{8a}$, $R^9$ and $R^{9a}$ are each hydrogen.

One embodiment of this embodiment are compounds wherein V is —C(O)—; $R^2$ is $C_7$-$C_{12}$aralkyl optionally substituted by one or more substituents selected from halo, cyano, nitro, hydroxy, $C_1$-$C_6$alkyl, $C_1$-$C_6$trihaloalkyl and $C_1$-$C_6$trihaloalkoxy; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

A further embodiment of this embodiment are compounds wherein $R^2$ is $C_7$-$C_{12}$aralkyl optionally substituted by one or more substituents selected from halo, $C_1$-$C_6$alkyl, $C_1$-$C_6$trihaloalkyl and $C_1$-$C_6$trihaloalkoxy; and $R^3$ is phenyl optionally substituted by one or more substituents selected from the group consisting of halo, $C_1$-$C_6$trihaloalkyl and $C_1$-$C_6$trihaloalkoxy.

Another embodiment of the above embodiment are compounds wherein V is —C(O)—; $R^2$ is $C_1$-$C_{12}$alkyl or $C_2$-$C_{12}$alkenyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^3$ is phenyl optionally substituted by one or more substituents selected from the group consisting of halo, $C_1$-$C_6$trihaloalkyl and $C_1$-$C_6$trihaloalkoxy.

In another embodiment of the invention, compounds of formula (Ia), as set forth above in the Summary of the Invention, are directed to compounds wherein x and y are each 1; W is —N($R^1$)—; V is —C(O)— or —C(S)—; $R^1$ is hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^4$ and $R^5$ are each hydrogen; and $R^6$, $R^{6a}$, $R^7$, $R^{7a}$, $R^8$, $R^{8a}$, $R^9$ and $R^{9a}$ are each hydrogen.

One embodiment of this embodiment are compounds wherein V is —C(O)—; $R^1$ is hydrogen or $C_1$-$C_6$alkyl; $R^2$ is $C_7$-$C_{12}$aralkyl optionally substituted by one or more substituents selected from halo, cyano, nitro, hydroxy, $C_1$-$C_6$alkyl, $C_1$-$C_6$trihaloalkyl and $C_1$-$C_6$trihaloalkoxy; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^2$)$_2$, —OC(O)$R^{12}$, —C(O)O$R^{12}$, S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^3$ is phenyl optionally substituted by one or more substituents selected from the group consisting of halo, $C_1$-$C_6$trihaloalkyl and $C_1$-$C_6$trihaloalkoxy.

Another embodiment of the above embodiment are compounds wherein V is —C(O)—; $R^1$ is hydrogen or $C_1$-$C_6$alkyl; $R^2$ is $C_1$-$C_{12}$alkyl, $C_2$-$C_{12}$alkenyl, $C_3$-$C_{12}$cycloalkyl or $C_4$-$C_{12}$cycloalkylalkyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

In another embodiment of the invention, compounds of formula (Ia), as set forth above in the Summary of the Invention, are directed to compounds wherein x and y are each 1; W is —N($R^1$)S(O)$_2$—; V is —C(O)— or —C(S)—; $R^1$ is hydrogen or $C_1$-$C_6$alkyl; $R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl; $R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl; $R^4$ and $R^5$ are each hydrogen; and $R^6$, $R^{6a}$, $R^7$, $R^{7a}$, $R^8$, $R^{8a}$, $R^9$ and $R^{9a}$ are each hydrogen.

One embodiment of this embodiment are compounds wherein V is —C(O)—; $R^1$ is hydrogen or $C_1$-$C_6$alkyl; $R^2$ is $C_1$-$C_{12}$alkyl, $C_2$-$C_{12}$alkenyl, $C_3$-$C_{12}$cycloalkyl or $C_4$-$C_{12}$cycloalkylalkyl; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

One embodiment of this embodiment are compounds wherein $R^2$ is $C_1$-$C_{12}$alkyl; and $R^3$ is phenyl optionally substituted by one or more substituents selected from the group consisting of halo, $C_1$-$C_6$trihaloalkyl and $C_1$-$C_6$trihaloalkoxy.

Another embodiment of the above embodiment are compounds wherein V is —C(O)—; $R^1$ is hydrogen or $C_1$-$C_6$alkyl; $R^2$ is $C_7$-$C_{12}$aralkyl optionally substituted by one or more substituents selected from halo, cyano, nitro, hydroxy, $C_1$-$C_6$alkyl, $C_1$-$C_6$trihaloalkyl and $C_1$-$C_6$trihaloalkoxy; $R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^2$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

Specific embodiments of the compounds of the invention are disclosed herein in the following Reaction Schemes and Examples.

In another embodiment, the methods of the invention are directed towards methods of treating a disease or condition mediated by stearoyl-CoA desaturase (SCD) in a mammal, wherein the method comprises administering to a mammal in need thereof a therapeutically effective amount of a compound of formula (Ia) as described above.

In another embodiment, the pharmaceutical compositions of the invention are directed towards pharmaceutical composition comprising a pharmaceutically acceptable excipient and a therapeutically effective amount of a compound of formula (Ia) as described above.

In another embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds of the Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome and the like, by administering to a patient in need of such treatment an effective amount of an SCD-modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 7. Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmlCrl-fa/fa) (available from Charles River Laboratories (Montréal, Quebec)).

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition includes but is not limited to a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport), hyperglycemia, low glucose tolerance, familial combined hyperlipidemia, coronary artery disease, atherosclerosis and its sequelae, heart disease, cerebrovascular disease (including but not limited to stroke, ischemic stroke and transient ischemic attack (TIA)), peripheral vascular disease, vascular restenosis, nephropathy, neuropathy, polycystic ovary syndrome, sleep-disorder breathing, and ischemic retinopathy. In a preferred embodiment, compounds of the invention will, in a patient, increase HDL levels and/or decrease triglyceride levels and/or decrease LDL or non-HDL-cholesterol levels.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin related diseases. In a preferred embodiment, compounds of the invention will be used to treat diabetes mellitus and obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including but not limited to eczema, acne, psoriasis, rosacea, keloid scar formation or prevention, diseases related to production or secretions from mucous membranes, such as monounsaturated fatty acids, wax esters, and the like.

An SCD-mediated disease or condition also includes inflammation, sinusitis, asthma, pancreatitis, osteoarthritis, rheumatoid arthritis, cystic fibrosis, and pre-menstrual syndrome.

An SCD-mediated disease or condition also includes but is not limited to a disease or condition which is, or is related to cancer (e.g. liver cancer), neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition which is, or is related to, neurological diseases, psychiatric disorders, multiple sclerosis, eye diseases, and immune disorders.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POTYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the C9-C10 desaturation of stearoyl-CoA) which is accomplished by delta-9 desaturases, such as stearoyl-CoA desaturase 1 (SCD1). As such these compounds inhibit the formation of various fatty acids and downstream metabolites thereof. This may lead to an accumulation of stearoyl-CoA or palmitoyl-CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 2 mg/Kg, 1 mg/Kg, or 0.5 mg/Kg and the target human dose is between 50 and 250 mg/70 Kg, although doses outside of this range may be acceptable. ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 µM, preferably below 1 µM and most preferably below 50 nM. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ in a 15 minute microsomal assay of preferably less than 10 µM, less than 5 µM, less than 2.5 µM, less than 1 µM, less than 750 nM, less than 500 nM, less than 250 nM, less than 100 nM, less than 50 nM, and most preferably less than 20 nM. The compound of the invention may show reversible inhibition (i.e., competitive inhibition) and preferably does not inhibit other iron binding proteins. The required dosage should preferably be no more than about once or twice a day or at meal times.

The identification of compounds of the invention as SCD inhibitors was readily accomplished using the SCD enzyme and microsomal assay procedure described in Brownlie et al, supra. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

These results provide the basis for analysis of the structure-activity relationship (SAR) between test compounds and SCD. Certain R groups tend to provide more potent inhibitory compounds. SAR analysis is one of the tools those skilled in the art may now employ to identify preferred embodiments of the compounds of the invention for use as therapeutic agents.

Other methods of testing the compounds disclosed herein are also readily available to those skilled in the art. Thus, in addition, said contacting may be accomplished in vivo. In one such embodiment, said contacting in step (a) is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1118:0 ratio); alternatively mice on a normal diet or mice with normal triglyceride levels may be used. Mouse models employing transgenic mice designed for hypertriglyceridemia are also available as is the mouse phenome database. Rabbits and hamsters are also useful as animal models, especially those expressing CETP (cholesteryl ester transfer protein).

Another suitable method for determining the in vivo efficacy of the compounds of the invention is to indirectly measure their impact on inhibition of SCD enzyme by measuring a subject's Desaturation Index after administration of the compound. "Desaturation Index" as employed in this specification means the ratio of the product over the substrate for the SCD enzyme as measured from a given tissue sample. This may be calculated using three different equations 18:1n-9/18:0 (oleic acid over stearic acid); 16:1n-7/16:0 (palmitoleic acid over palmitic acid); and/or 16:1n-7+18:1n-7/16:0 (measuring all reaction products of 16:0 desaturation over 16:0 substrate). Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art know how to determine suitable doses of the compounds for use in treating the diseases and disorders contemplated herein. Therapeutic doses are generally identified through a dose ranging study in humans based on preliminary evidence derived from animal studies. Doses must be sufficient to result in a desired therapeutic benefit without causing unwanted side-effects for the patient. The preferred dosage range for an animal is 0.001 mg/Kg to 10,000 mg/Kg, including 0.5 mg/Kg, 1.0 mg/Kg and 2.0 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

Preparation of the Compounds of the Invention

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Although anyone skilled in the art is capable of preparing the compounds of the invention according to the general techniques disclosed above, more specific details on synthetic techniques for compounds of the invention are provided elsewhere in this specification for convenience. Again, all reagents and reaction conditions employed in synthesis are known to those skilled in the art and are available from ordinary commercial sources.

The following Reaction Schemes illustrate methods to make compounds of this invention. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. In the following Reaction Schemes x, y, $R^1$, $R^2$, $R^3$, $R^4$, $R^5$, $R^6$, $R^{6a}$, $R^7$, $R^{7a}$, $R^8$, $R^{8a}$, $R^9$ and $R^{9a}$ are as defined as in the Specification unless specifically defined otherwise; X is selected from Cl or Br; and PG is a protecting group, such as BOC, benzyl and the like.

In general, the compounds of formula (I) of this invention where W is S and V is —C(O)—, —S(O)$_2$— or —C($R^{11}$)H— can be synthesized following the general procedure as described in Reaction Scheme 1.

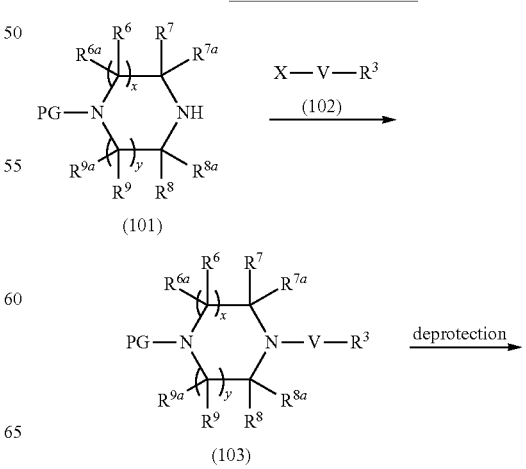

REACTION SCHEME 1

-continued

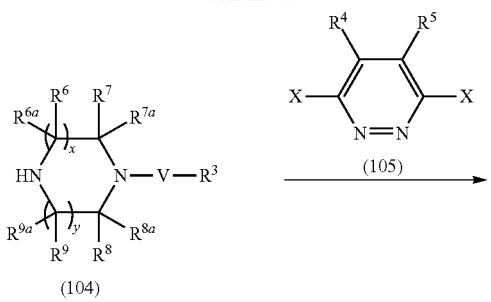

(104)

(105)

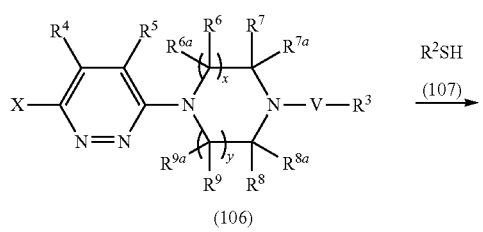

Formula (I)

Compound 106. The mixture of a pyridazine compound of formula (105) (1 equivalent) and the compound of formula (104) obtained above (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (106).

Compound of formula (I). A mixture of compound (106) (1 equivalent), a thiol compound of formula (107) (1 equivalent) and a base, such as, but not limited to, sodium hydroxide (1 equivalent) in an anhydrous solvent, such as, but not limited to, tetrahydrofuran, 1,4-dioxane, is refluxed for 8-12 h. The reaction mixture is cooled, diluted with water, acidified, then extracted with an organic solvent, such as, but not limited to, dichloromethane. The organic layer is separated and dried over anhydrous $MgSO_4$ to yield compound of formula (I) where W is —S— and V is —C(O)—, —S(O)$_2$— or —C($R^{11}$)H—.

Alternatively, the compounds of formula (I) of this invention where W is —O— and V is —C(O)—, —S(O)$_2$— or —C($R^{11}$)H— can be synthesized following the general procedure as described in Reaction Scheme 2.

REACTION SCHEME 2

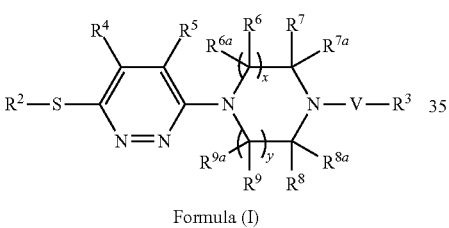

(106)

$R^1OH$
(108)

Formula (I)

The starting materials for the above reaction scheme are commercially available or can be prepared according to methods known to one skilled in the art or by methods disclosed herein. In general, the compounds of the invention are prepared in the above reaction scheme as follows:

Compound 103. To a stirred solution of the amine of formula (101) (1 equivalent) in a solvent such as dichloromethane or toluene is added the solution of a compound of formula (102) (1 equivalent) in a solvent such as dichloromethane or toluene in the presence of a base such as triethylamine or Hunigs base. The resulting mixture is stirred at ambient temperature for an adequate time period and then quenched with water. The organic phase is washed with $H_2O$, brine, dried over and then concentrated in vacuo to afford the product of formula (103).

Compound 104. A solution of compound of formula of (103) obtained above is dissolved in an adequate solvent and the protecting group PG is removed under standard deprotection conditions such as hydrolysis or hydrogenation to obtain the amine of formula (104).

The starting materials for the above reaction scheme are commercially available or can be prepared according to methods known to one skilled in the art or by methods disclosed herein. In general, the compounds of the invention are prepared in the above reaction scheme as follows:

Compound of formula (I). To a mixture of compound (106) (1 equivalent) and an alcohol of formula (108) (1 equivalent) in an anhydrous solvent, such as, but not limited to, benzene or toluene is added 60% NaH (1 equivalent). The reaction mixture is refluxed for 1-4 h with stirring, then cooled to ambient temperature, diluted with water and extracted with an organic solvent, such as, but not limited to, ethyl acetate or dichloromethane. The organic layer is separated, washed with water, dried over anhydrous $MgSO_4$, filtered and concentrated. Purification by column chromatography affords the compound of formula (I) where W is —O— and V is —C(O)—, —S(O)$_2$— or —C($R^{11}$)H—

Alternatively, the compounds of formula (I) of this invention where W is —$NR^1$— and V is —C(O)—, —S(O)$_2$— or —C($R^{11}$)H— can be synthesized following the general procedure as described in Reaction Scheme 3.

REACTION SCHEME 3

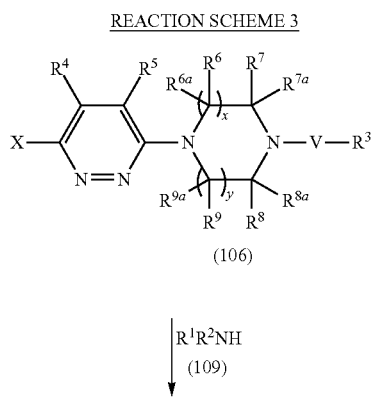

(106)

$R^1R^2NH$
(109)

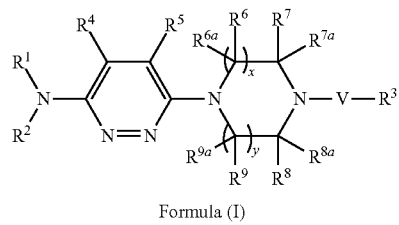

Formula (I)

The starting materials for the above reaction scheme are commercially available or can be prepared according to methods known to one skilled in the art or by methods disclosed herein. In general, the compounds of the invention are prepared in the above reaction scheme as follows:

Compound of formula (I). To a stirred solution of compound (106) (1 equivalent) and an amine of formula (109) (1.5-2 equivalent) in an organic solvent, such as, but not limited to, acetone or n-butanol is added 2-3 equivalent of acid in water. The reaction is refluxed for 8-16 h while stirring, then cooled to ambient temperature and the solvent is removed in vacuo. Purification by purified by column chromatography affords the compound of formula (I) where W is —$NR^1$— and V is —C(O)—, —S(O)$_2$— or —C($R^{11}$)H—.

Alternatively, the compounds of formula (I) of this invention where W is —S(O)$_t$— (where t=1 or 2) and V is —C(O)—, —S(O)$_2$— or —C($R^{11}$)H— can be synthesized following the general procedure as described in Reaction Scheme 4.

REACTION SCHEME 4

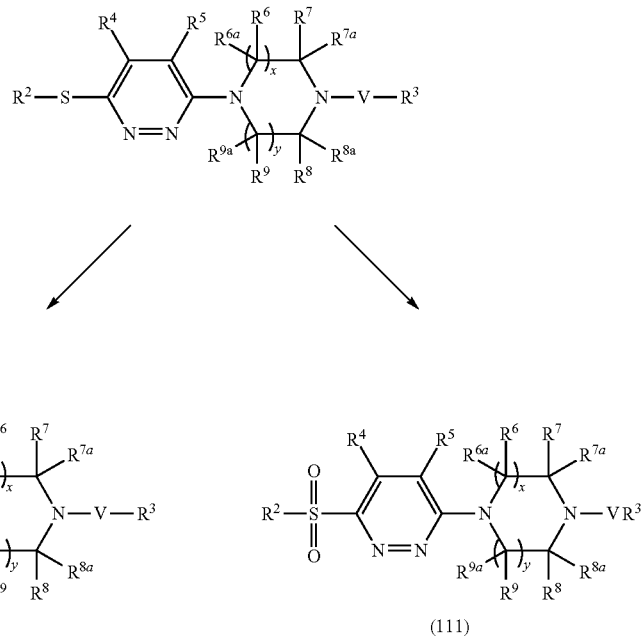

The starting materials for the above reaction scheme are commercially available or can be prepared according to methods known to one skilled in the art or by methods disclosed herein. In general, the compounds of the invention are prepared in the above reaction scheme as follows:

Compound (110). To a solution of sodium periodate (1 equivalent) in an appropriate solvent, such as, but not limited to, MeOH and water mixture is added the thioether compound (1 equivalent). The reaction mixture is stirred in an ice-bath for 4-8 hours and then diluted with an organic solvent, such as, but not limited to, dichloromethane. The organic layer is separated and washed with water, dried over anhydrous $Na_2SO_4$, concentrated in vacuo. Purification by column chromatography affords the compound (110).

Compound (111). A mixture of the thioether compound (1 equivalent) and an oxidizing agent, such as, but not limited to, m-CPBA (2-4 equivalent) in an appropriate solvent, such as, but not limited to, dichloromethane is stirred in an ice-bath for 2-4 h, and the stirring is continued for another 12-24 hours. The reaction mixture is diluted with an organic solvent such as dichloromethane, washed with a basic solution, such as NaOH solution, and brine. Organic layer is separated and dried over anhydrous $Na_2SO_4$, then concentrated in vacuo. Purification by column chromatography yields the compound (111).

Alternatively, the compounds of formula (I) of the invention where W is —NH— and V is —C(O)—, —S(O)$_2$— or —C(R$^{11}$)H— can be synthesized following the general procedure as described in Reaction Scheme 5.

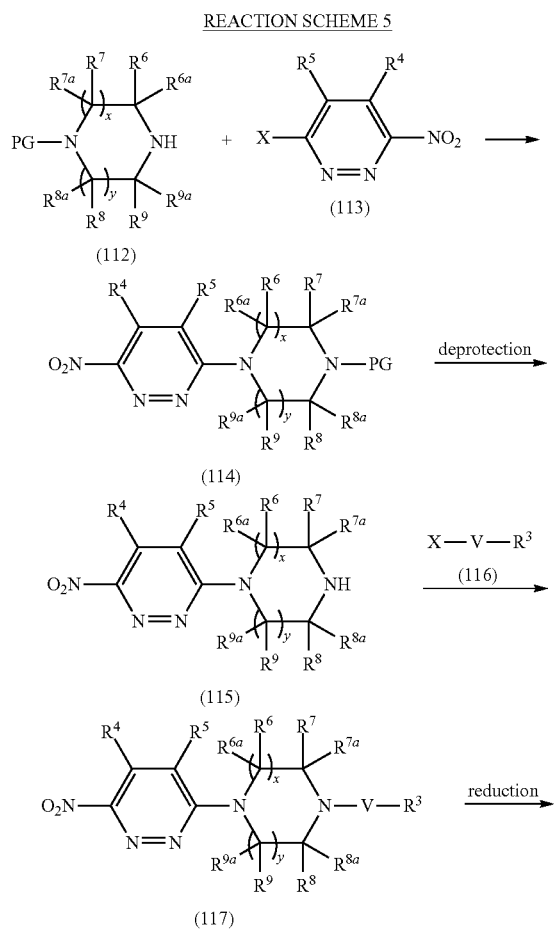

REACTION SCHEME 5

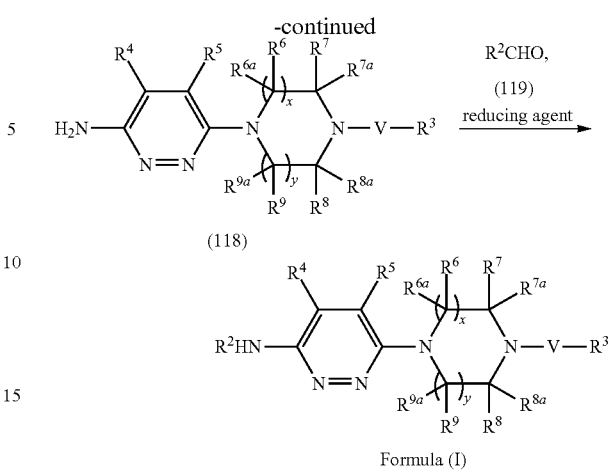

Formula (I)

The starting materials for the above reaction scheme are commercially available or can be prepared according to methods known to one skilled in the art or by methods disclosed herein. In general, the compounds of the invention are prepared in the above reaction scheme as follows:

Compound 114. To a stirred solution of the amine of formula (112) (1 equivalent) in a solvent such as dichloromethane or toluene is added the solution of a chloride of formula (113) (1 equivalent) in a solvent such as dichloromethane or toluene in the presence of a base such as triethylamine or Hunigs base. The resulting mixture is stirred at ambient temperature for an adequate time period and then quenched with water. The organic phase is washed with $H_2O$, brine, dried over and then concentrated in vacuo to afford the product of formula (114).

Compound 115. A solution of compound of formula of (114) obtained above is dissolved in an adequate solvent and the protection group PG is removed under standard deprotection conditions such as hydrolysis or hydrogenation to obtain the amine of formula (115).

Compound 117. The mixture of a pyridine compound of formula (115) (1 equivalent) and the compound of formula (116) (1.5 equivalent) in an adequate solvent is heated at reflux for 4-24 hours. To the reaction mixture is added a basic solution such as NaOH solution. The aqueous layer is extracted by an organic solvent such as dichloromethane or ethyl acetate. The combined organic phase is dried, then evaporated to dryness. The crude compound is purified by column chromatography or crystallization to afford the compound of formula (117).

Compound 118. The nitro compound of formula (117) can be reduced to the corresponding amine compound of formula (118) using a standard hydrogenation process known to one skilled in the art.

Compound of formula (I). Reaction of amine (118) with an appropriate aldehyde of formula (119) in the presence of a reducing agent such as, but not limited to, sodium borohydride in a solvent such as, but not limited, ethanol affords the compound of formula (I) where W is —NH— and V is —C(O)—, —S(O)$_2$— or —C(R$^{11}$)H—.

Alternatively, the compounds of formula (I) of the invention where W is —O— and V is —C(O)—, —S(O)$_2$— or —C(R$^{11}$)H— can be synthesized following the general procedure as described in Reaction Scheme 6.

REACTION SCHEME 6

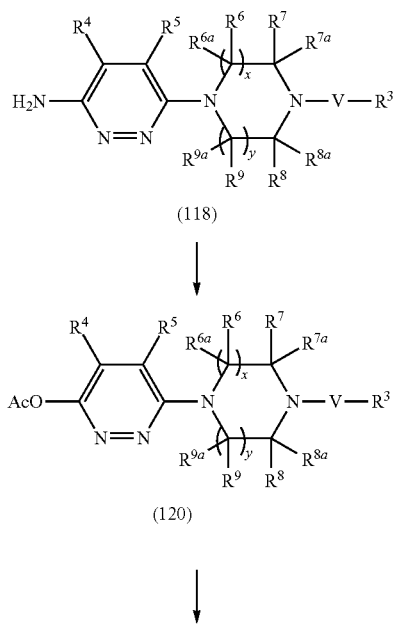

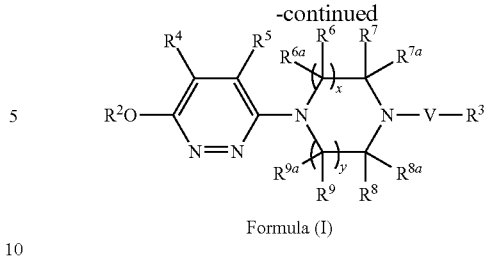

Formula (I)

Reaction of amine (118) with sodium nitrite in the presence of a Lewis acid such as, but not limited to, boron trifluoride diethyl etherate in a solvent such as, but not limited to, N,N-dimethylformamide, generates a diazonium intermediate that can be converted into the acetoxy compound (120) by quenching the above reaction mixture with acetic anhydride. Hydrolysis of the ester compound (120) in the presence of a base such as, but not limited to, sodium hydroxide, produces a hydroxy intermediate that can be converted into the desired product of formula (I) (W=—O—) with an appropriate $R^2X$ in the presence of a base such as, but not limited to, sodium hydride in a solvent such as, but not limited to, tetrahydrofuran or N,N-dimethylformamide.

Alternatively, the compounds of formula (I) of the invention where W is —S(O)$_t$ (where t is 0, 1 or 2) and V is —C(O)—, —S(O)$_2$— or —C(R$^{11}$)H— can be synthesized following the general procedure as described in Reaction Scheme 7.

REACTION SCHEME 7

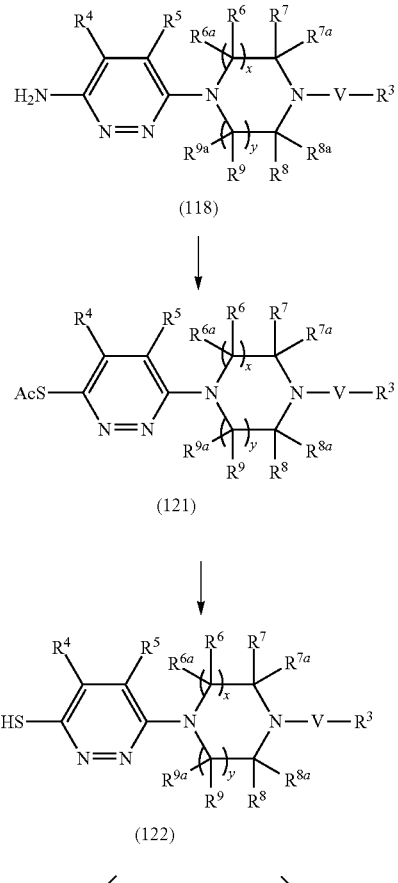

-continued

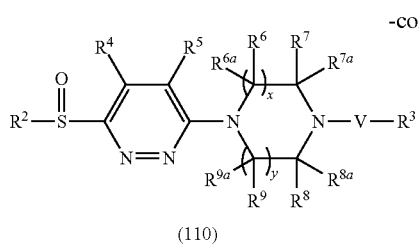

(110)

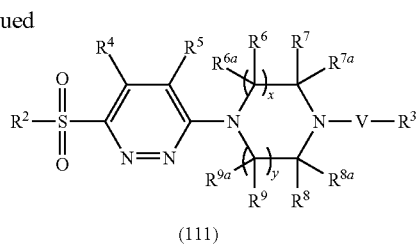

(111)

Reaction of amine (118) with sodium nitrite in the presence of a Lewis acid such as, but not limited to, boron trifluoride diethyl etherate in a solvent such as, but not limited to, N,N-dimethylformamide, generates a diazonium intermediate that can be converted into compound (121) by quenching the above reaction mixture with acetyl sulfide. Hydrolysis of the thioester compound (121) in the presence of a base such as, but not limited to, sodium hydroxide, produces a thiol intermediate that can be converted into the desired sulfide product (122) (formula (I), W=—S—) with an appropriate $R^2X$ in the presence of a base such as, but not limited to, sodium hydride in a solvent such as, but not limited to, tetrahydrofuran, 1,4-dioxane or N,N-dimethylformamide. Treatment of compound (122) with an oxidizing agent such as, but not limited to, sodium periodate in a mixture of methanol and water affords the sulfoxide compound (110) (formula (I), W=—S(O)—). Alternatively, the sulfide compound (122) can be treated with trifluoro acetic anhydride and hydrogen peroxide in a solvent such as, but not limited to, dichloromethane to give the sulfone product (111) (formula (I), W=—S(O)$_2$—).

PREPARATION 1

Synthesis of [4-(6-CHLOROPYRIDAZIN-3-YL) PIPERAZIN-1-YL](2-TRIFLUOROMETHYLPHENYL)METHANONE A. To a stirred solution of 1-Boc-piperazine (1.96 g, 10.5 mmol) in dichloromethane (50 mL) was added 2-trifluoromethylbenzoyl chloride (2.09 g, 10.0 mmol) as a dichloromethane solution in the presence of triethylamine (3 mL) at 0° C. The resulting mixture was stirred at ambient temperature for 18 hours and then quenched with water (25 mL). The organic phase was washed with water, saturated NaCl, dried over MgSO$_4$ and then concentrated in vacuo to afford the desired product as a pall yellow solid used for next step reaction without further purification.

B. A solution of the compound obtained above (10 mmol) in 50 mL of a 1:4 mixture of trifluoroacetic acid and dichloromethane was stirred at ambient temperature for 5 h. After concentration in vacuo the residue was dissolved in dichloromethane (100 mL) and washed sequentially with 1 N NaOH (10 mL), water, saturated NaCl, and then dried over MgSO$_4$, filtered and concentrated in vacuo to yield piperazin-1-yl-(2-trifluoromethylphenyl)methanone as a light yellow oil. This oil was converted into HCl salt by the addition of 10 mL of 2 N HCl in ether and 100 mL of anhydrous ether to the solution of the compound in 10 mL of dichloromethane. The white solid formed was filtered and dried to yield the HCl salt.

C. A mixture of 3,6-dichloropyridazine (0.25 g, 1.678 mmol), piperazin-1-yl-(2-trifluoromethylphenyl)methanone (1.483 g, 5.034 mmol) obtained above, water (0.85 mL) and hydrochloric acid (37%, 0.035 mL) was heated to 80-100° C. for 36 h. The reaction mixture was cooled to room temperature, concentrated in vacuo, diluted with water. The pH of the mixture was brought to pH 11 with 2 N NaOH solution and the mixture was then extracted with diethyl ether (3×15 mL). The organic layer was dried and concentrated in vacuo. The residue was purified by column chromatography to yield a white solid (0.236 g, 38% yield).

EXAMPLE 1

Synthesis of {4-[6-(METHYLPHENETHYLAMINO)PYRIDAZIN-3-YL]PIPERAZIN-1-YL}-(2-TRIFLUOROMETHYLPHENYL)METHANONE A mixture of [4-(6-chloropyridazin-3-yl)piperazin-1-yl]-(2-trifluoromethylphenyl)methanone (0.072 g, 0.194 mmol), N-methyl-2-phenylethylamine (0.052 g, 0.388 mmol), ammonium chloride (0.01 g, 0.194 mmol) in n-butanol (4 mL) was refluxed for 48 hours. The reaction mixture was cooled to room temperature, then added 10% potassium carbonate solution, and extracted with ethyl acetate. The organic extract was dried over anhydrous Na$_2$SO$_4$, and then concentrated in vacuo. The residue was purified by column chromatography to yield the title compound as a white solid (10 mg, 11% yield). $^1$H NMR (400 MHz, CDC$_3$) δ 7.73, 7.61-7.64, 7.53-7.56, 7.36, 7.26-7.29, 7.19-7.21, 6.91, 6.75, 3.95, 3.75, 3.30-3.50, 0.92. MS (ES+) m/z 470.3 (M+1).

EXAMPLE 1.1

Synthesis of [4-(6-PHENETHYLAMINOPYRIDAZIN-3-YL)PIPERAZIN-1-YL]-(2-TRIFLUOROMETHYLPHENYL)METHANONE Following the procedure set forth above in Example 1, only making variations using 2-phenylethylamine to replace N-methyl-2-phenylethylamine to react with [4-(6-chloropyridazin-3-yl)piperazin-1-yl]-(2-trifluoromethylphenyl) methanone, the title compound was obtained as a white solid (11.8 mg, 15% yield). $^1$H NMR (CDCl$_3$, 400 MHz) δ 7.74, 7.62-7.68, 7.52-7.57, 7.33-7.37, 7.28-7.32, 7.40-7.46, 6.83, 6.18, 3.95, 3.68-3.70, 3.30-3.50, 2.96. MS (ES+) m/z 456.4 (M+1).

EXAMPLE 2

Synthesis of PROPANE-1-SULFONIC ACID {6-[4-(2-TRIFLUOROMETHYLBENZOYL)PIPERAZIN-1-YL]PYRIDAZIN-3-YL}AMIDE To a mixture of [4-(6-amino pyridazin-3-yl)piperazin-1-yl]-(2-trifluoromethylphenyl)methanone (0.10 g, 0.285 mmol) and triethyl amine (0.037 g, 0.371 mmol) in 10 mL of dichloromethane at 0° C. was added n-propylsulphonyl chloride (0.044 g, 0.313 mmol). The reaction mixture was stirred at room temperature for 4 hours and then dilute hydrochloric acid solution was added (20 mL). The mixture was extracted with dichloromethane. The organic layer was washed with brine, dried over anhydrous sodium sulphate, the concentrated in vacuo. The residue was purified by column chromatography to yield the title compound as a white solid (46.3 mg, 35.5% yield). $^1$H NMR (400 MHz, CDCl$_3$) δ 7.75, 7.63-7.66, 7.56-7.59, 7.37, 7.25, 6.99, 4.04-4.07, 3.85-3.89, 3.71-3.78, 3.35, 1.96-2.00, 1.1.

EXAMPLE 3

Synthesis of {4-[6-(2-PHENYLETHANESULFO-NYL)PYRIDAZIN-3-YL]PIPERAZIN-1-YL}-(2-TRIFLUOROMETHYL-PHENYL)METHANONE A mixture of m-CPBA (0.044 g, 0.26 mmol) and [4-(6-phenethylsulfanylpyridazin-3-yl)piperazin-1-yl]-(2-trifluoromethylphenyl)methanone in 2.5 mL of dichloromethane was stirred at room temperature over night. The reaction mixture was washed with 1N NaOH solution, extracted with dichloromethane. The residue obtained after removal of solvent was purified by column chromatography to yield the title compound as a white solid (21 mg, 16.2% yield). $^1$H NMR (400 MHz, CDCl$_3$) δ 7.83, 7.76, 7.64-7.66, 7.57-7.59, 7.38, 7.23-7.25, 7.215-7.20, 6.94, 4.07-4.10, 3.74-3.93, 3.30-3.40, 3.12-3.15.

EXAMPLE 4

Synthesis of {4-[6-(2-PHENYLETHANESULFI-NYL)PYRIDAZIN-3-YL]PIPERAZIN-1-YL}-(2-TRIFLUOROMETHYLPHENYL)METHANONE To an ice-cold solution of sodium periodate (0.025 g, 0.12 mmol) in 1:1 mixture of water and methanol was added [4-(6-phenethylsulfanylpyridazin-3-yl)piperazin-1-yl]-(2-trifluoromethylphenyl)methanone. The reaction mixture was stirred at room temperature over night, diluted with water and then extracted with dichloromethane. The organic layer was washed with water, dried over anhydrous MgSO$_4$ and then concentrated in vacuo. The residue was purified by column chromatography to yield the title compound as a white solid (41 mg, 69.2%). $^1$H NMR (400 MHz, CDCl$_3$) δ 7.86, 7.75, 7.63-7.66, 7.56-7.59, 7.37, 7.25-7.28, 7.21-7.17, 7.07-7.09, 4.04-4.10, 3.83-3.91, 3.70-3.80, 3.45-3.35, 3.26-3.30, 3.2-3.15.

EXAMPLE 5

Synthesis of [4-(6-PHENETHYLOXYPYRIDAZIN-3-YL)PIPERAZIN-1-YL]-(2-TRIFLUOROM-ETHYL-PHENYL)METHANONE A mixture of [4-(6-chloropyridazin-3-yl)piperazin-1-yl]-(2-trifluoromethylphenyl)methanone (0.075 g, 0.202 mmol), 2-phenylethanol (0.025 g, 0.202 mmol) and sodium hydride (0.010 g) in 5 mL of toluene was stirred at room temperature for 1 hour, and then refluxed overnight. The reaction mixture was cooled to room temperature, added 20 mL of water, and then extracted with ethyl acetate. The organic layer was washed with water, dried over anhydrous sodium sulphate, concentrated in vacuo. The residue was purified by column chromatography to yield the title compound as a white solid (58 mg, 62.9%). $^1$H NMR (400 MHz, CDCl$_3$) δ 7.73, 7.61-7.64, 7.53-7.56, 7.36, 7.22-7.30, 7.20-7.24, 7.02, 6.86, 4.64, 3.91-3.98, 3.57, 3.48-3.52, 3.32, 3.11.

EXAMPLE 5.1

Synthesis of {4-[6-(2-CYCLOPROPYLETHOXY)PYRIDAZIN-3-YL]PIPERAZIN-1-YL}-(2-TRIFLUOROMETHYLPHENYL)METHANONE Following the procedure set forth above in Example 5, only making variations using 2-cyclopropylethanol to replace 2-phenylethanol to react with [4-(6-chloropyridazin-3-yl)piperazin-1-yl]-(2-trifluoromethylphenyl)methanone, the title compound was obtained as a white solid (56 mg, 74.8% yield). $^1$H NMR (400 MHz, CDCl$_3$) δ 7.72, 7.60-7.63, 7.52-7.56, 7.35, 7.03, 6.87, 4.46, 3.91-3.98, 3.55, 3.46-3.50, 3.31, 1.68, 0.79-0.84, 0.43-0.46, 0.11--0.79.

EXAMPLE 6

Synthesis of [4-(6-PHENETHYLSULFANYLPY-RIDAZIN-3-YL)PIPERAZIN-1-YL](2-TRIFLUO-ROMETHYLPHENYL)METHANONE A mixture of [4-(6-chloro pyridazin-3-yl)piperazin-1-yl]-(2-trifluoromethylphenyl)methanone (0.089 g, 0.240 mmol), 2-phenylethanethiol (0.049 g, 0.36 mmol) and sodium hydroxide (9.6 mg) in 5 mL 1,4-dioxane was heated at 100-110° C. overnight. The reaction mixture was cooled to room temperature, diluted with 20 mL of water, and then extracted with dichloromethane. The organic layer was washed with water, dried over anhydrous sodium sulphate, then concentrated in vacuo. The residue was purified by column chromatography to yield the title compound as a white solid (50 mg, 43.7% yield). $^1$H NMR (400 MHz, CDCl$_3$) δ 7.65, 7.52-7.55, 7.47-7.48, 7.27, 7.12-7.22, 7.03, 6.76, 3.89-3.94, 3.79-3.84, 3.54-3.61, 3.49-3.51, 3.45, 3.17-3.25, 2.97.

EXAMPLE 6.1

Synthesis of {4-[6-(3-METHYLBUTYLSULFA-NYL)PYRIDAZIN-3-YL]PIPERAZIN-1-YL}-(2-TRIFLUOROMETHYL-PHENYL)METHANONE Following the procedure set forth above in Example 6, only making variations using 3-methylbutane-1-thiol to replace 2-phenylethanethiol to react with [4-(6-chloropyridazin-3-yl)piperazin-1-yl]-(2-trifluoromethylphenyl)methanone, the title compound was obtained as a white solid (24.3 mg, 26.4% yield). $^1$H NMR (400 MHz, CDCl$_3$) δ 8.04, 7.98, 6.99, 3.79, 3.56, 3.45-3.47, 3.40, 1.85-1.87, 1.52, 0.72-0.80, 0.46-0.48, 0.09-0.10.

EXAMPLE 7

Measuring Stearoyl-CoA Desaturase Inhibition Activity of a Test Compound Using Mouse Liver Microsomes The identification of compounds of the invention as SCD inhibitors was readily accomplished using the SCD enzymes and microsomal assay procedure described in Brownlie et al, PCT published patent application, WO 01/62954.

Preparation of Mouse Liver Microsomes:

Male ICR mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1:3 w/v) containing 0.25 M sucrose, 62 mM potassium phosphate buffer (pH 7.0), 0.15 M KCl, 1.5 mM N-acetyleysteine, 5 mM $MgCl_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Reactions are started by adding 2 mg of microsomal protein to pre-incubated tubes containing 0.20 μCi of the substrate fatty acid (1-$^{14}$C palmitic acid) at a final concentration of 33.3 μM in 1.5 ml of homogenization solution, containing 42 mM NaF, 0.33 mM niacinamide, 1.6 mM ATP, 1.0 mM NADH, 0.1 mM coenzyme A and a 10 μM concentration of test compound. The tubes are vortexed vigorously and after 15 min incubation in a shaking water bath (37° C.), the reactions are stopped and fatty acids are analyzed.

Fatty acids are analyzed as follows: The reaction mixture is saponified with 10% KOH to obtain free fatty acids which are further methylated using $BF_3$ in methanol. The fatty acid methyl esters are analyzed by high performance liquid chromatography (HPLC) using a Hewlett Packard 1090, Series II chromatograph equipped with a diode array detector set at 205 nm, a radioisotope detector (Model 171, Beckman, Calif.) with a solid scintillation cartridge (97% efficiency for $^{14}$C-detection) and a reverse-phase ODS (C-18) Beckman column (250 mm×4.6 mm i.d.; 5 μm particle size) attached to a pre-column with a μBondapak C-18 (Beckman) insert. Fatty acid methyl esters are separated isocratically with acetonitrile/water (95:5 v-v) at a flow rate of 1 mL/min and are identified by comparison with authentic standards. Alternatively, fatty acid methyl esters may be analyzed by capillary column gas-chromatography (GC) or Thin Layer Chromatography (TLC).

Those skilled in the art are aware of a variety of modifications to this assay that can be useful for measuring inhibition of stearoyl-CoA desaturase activity in microsomes by test compounds.

Using this and modified assays, compounds of the invention have been found to be effective SCD inhibitors. Data for representative compounds of the invention are shown in the following Tables 1 and 2. The activity was defined in terms of % SCD enzyme activity remaining at the desired concentration of the test compound, or as $IC_{50}$ values.

All of the U.S. patents, U.S. patent application publications, U.S. patent applications, foreign patents, foreign patent applications and non-patent publications referred to in this specification are incorporated herein by reference, in their entirety.

TABLE 1

| Chemical Name | Chemical Structure | Microsome $IC_{50}$ (μM) | Cell $IC_{50}$ (μM) |
|---|---|---|---|
| [4-(6-Phenethylsulfanyl-pyridazin-3-yl)-piperazin-1-yl]-(2-trifluoromethyl-phenyl)-methanone | 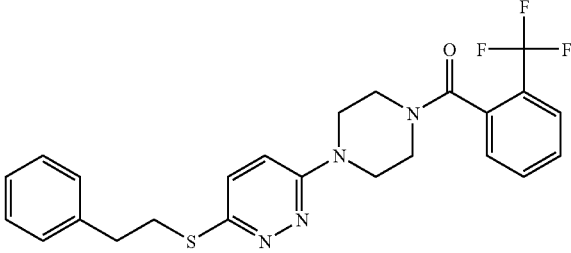 Example 6 | 0.060 | 0.033 |
| {4-[6-(2-Phenyl-ethanesulfinyl)-pyridazin-3-yl]-piperazin-1-yl}-(2-trifluoromethyl-phenyl)-methanone | 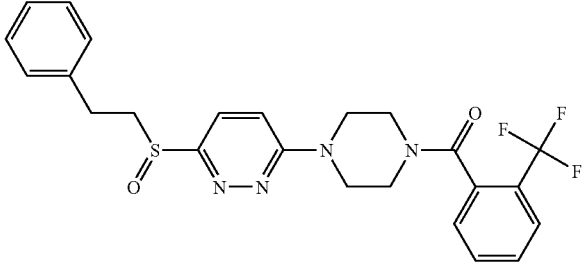 Example 4 | 0.067 | 0.175 |

TABLE 1-continued

| Chemical Name | Chemical Structure | Microsome IC$_{50}$ (μM) | Cell IC$_{50}$ (μM) |
|---|---|---|---|
| {4-[6-(2-Phenyl-ethanesulfonyl)-pyridazin-3-yl]-piperazin-1-yl}-(2-trifluoromethyl-phenyl)-methanone | Example 3 | 0.067 | 0.111 |
| {4-[6-(3-Methyl-butylsulfanyl)-pyridazin-3-yl]-piperazin-1-yl}-(2-trifluoromethyl-phenyl)-methanone | Example 6.1 | 0.447 | 0.849 |
| [4-(6-Phenethyloxy-pyridazin-3-yl)-piperazin-1-yl]-(2-trifluoromethyl-phenyl)-methanone | Example 5 | 4.555 | 4.300 |
| Propane-1-sulfonic acid {6-[4-(2-trifluoromethyl-benzoyl)-piperazin-1-yl]-pyridazin-3-yl}-amide | Example 2 | 6.250 | 10.527 |

TABLE 2

| Chemical Name | Chemical Structure | Residual Activity (% remaining, 1 μM) | Residual Activity (% remaining, 10 μM) |
| --- | --- | --- | --- |
| {4-[6-(2-Cyclopropyl-ethoxy)-pyridazin-3-yl]-piperazin-1-yl}-(2-trifluoromethyl-phenyl)-methanone | Example 5.1 | 53.875 Projected $IC_{50}$ = 1-10 μM | 29.330 |
| [4-(6-Phenethylamino-pyridazin-3-yl)-piperazin-1-yl]-(2-trifluoromethyl-phenyl)-methanone | Example 1.1 | 91.144 Projected $IC_{50}$ = 10-50 μM | 55.946 |
| {4-[6-(Methyl-phenethyl-amino)-pyridazin-3-yl]-piperazin-1-yl}-(2-trifluoromethyl-phenyl)-methanone | Example 1 | 86.210 Projected $IC_{50}$ = 10-50 μM | 57.955 |

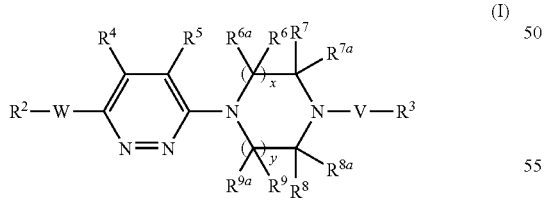

What is claimed is:

1. A method of inhibiting stearoyl-CoA desaturase-1 (SCD-1) in a mammal, wherein the method comprises administering to the mammal an effective amount of a compound of formula (I):

(I)

$R^2$—W—[pyridazine-piperazine structure with $R^4$, $R^5$, $R^{6a}$, $R^6$, $R^7$, $R^{7a}$, $R^{8a}$, $R^8$, $R^9$, $R^{9a}$]—N—V—$R^3$ wherein:

x and y are each independently 1;

W is —O—, —C(O)O—, —N($R^1$)—, —S(O)$_t$— (where t is 0, 1 or 2), —N($R^1$)S(O)$_2$—, —OC(O)— or —C(O)—;

V is —C(O)—, —C(S)—, —C(O)N($R^1$)—, —C(O)O—, —S(O)$_2$—, or —S(O)$_2$N($R^1$);

each $R^1$ is independently selected from the group consisting of hydrogen, $C_1$-$C_{12}$alkyl, $C_2$-$C_{12}$hydroxyalkyl, $C_4$-$C_{12}$cycloalkylalkyl and $C_7$-$C_{19}$aralkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

or $R^2$ is a multi-ring structure having 2 to 4 rings wherein the rings are independently selected from the group consisting of cycloalkyl, heterocyclyl, aryl and heteroaryl and where some or all of the rings may be fused to each other;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

or $R^3$ is a multi-ring structure having 2 to 4 rings wherein the rings are independently selected from the group consisting of cycloalkyl, heterocyclyl, aryl and heteroaryl and where some or all of the rings may be fused to each other;

$R^4$ and $R^5$ are each independently selected from hydrogen, fluoro, chloro, methyl, methoxy, trifluoromethyl, cyano, nitro or —N($R^{13}$)$_2$;

$R^6$, $R^{6a}$, $R^7$, $R^{7a}$, $R^8$, $R^{8a}$, $R^9$ and $R^{9a}$ are each independently selected from hydrogen or $C_1$-$C_3$alkyl; and each $R^{13}$ is independently selected from hydrogen or $C_1$-$C_6$alkyl;

a stereoisomer, enantiomer or tautomer thereof, a pharmaceutically acceptable salt thereof, a pharmaceutical composition thereof or a prodrug thereof.

2. The method of claim 1, wherein the mammal is a human.

3. The method of claim 1, wherein the mammal has dyslipidemia, or hypertriglyceridemia.

4. The method of claim 1, wherein:
x and y are each 1;
W is —O—;
V is —C(O)— or —C(S)—;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{19}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
$R^4$ and $R^5$ are each hydrogen; and
$R^6$, $R^{6a}$, $R^7$, $R^{7a}$, $R^8$, $R^{8a}$, $R^9$ and $R^{9a}$ are each hydrogen.

5. The method of claim 4, wherein:
V is —C(O)—;
$R^2$ is $C_7$-$C_{12}$aralkyl optionally substituted by one or more substituents selected from halo, cyano, nitro, hydroxy, $C_1$-$C_6$alkyl, $C_1$-$C_6$trihaloalkyl or $C_1$-$C_6$trihaloalkoxy;
$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N(R$^{12}$)$_2$, —OC(O)R$^{12}$, —C(O)OR$^{12}$, —S(O)$_2$N(R$^{12}$)$_2$, cycloalkyl, heterocyclyl, heteroaryl and heteroarylcycloalkyl; and
each $R^{12}$ is independently selected from hydrogen, $C_1$-$C_6$alkyl, $C_3$-$C_6$cycloalkyl, aryl or aralkyl.

6. The method of claim 5, wherein:
$R^2$ is $C_7$-$C_{12}$aralkyl optionally substituted by one or more substituents selected from halo, $C_1$-$C_6$alkyl, $C_1$-$C_6$trihaloalkyl or $C_1$-$C_6$trihaloalkoxy; and
$R^3$ is phenyl optionally substituted by one or more substituents selected from the group consisting of halo, $C_1$-$C_6$trihaloalkyl and $C_1$-$C_6$trihaloalkoxy.

7. The method of claim 6, wherein the compound is [4-(6-Phenethyloxy-pyridazin-3-yl)-piperazin-1-yl]-(2-trifluoromethyl-phenyl)-methanone.

8. The method of claim 4, wherein:
V is —C(O)—;
$R^2$ is $C_1$-$C_{12}$alkyl or $C_2$-$C_{12}$alkenyl;
$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N(R$^{12}$)$_2$, —OC(O)R$^{12}$, —C(O)OR$^{12}$, —S(O)$_2$N(R$^{12}$)$_2$, cycloalkyl, heterocyclyl, heteroaryl and heteroarylcycloalkyl; and
each $R^{12}$ is independently selected from hydrogen, $C_1$-$C_6$alkyl, $C_3$-$C_6$cycloalkyl, aryl or aralkyl.

9. The method of claim 4, wherein:
V is —C(O)—;
$R^2$ is $C_3$-$C_{12}$cycloalkyl or $C_4$-$C_{12}$cycloakylalkyl;
$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N(R$^{12}$)$_2$, —OC(O)R$^{12}$, —C(O)OR$^{12}$, —S(O)$_2$N(R$^{12}$)$_2$, cycloalkyl, heterocyclyl, heteroaryl and heteroarylcycloalkyl; and
each $R^{12}$ is independently selected from hydrogen, $C_1$-$C_6$alkyl, $C_3$-$C_6$cycloalkyl, aryl or aralkyl.

10. The method of claim 9, wherein:
$R^2$ is $C_4$-$C_{12}$cycloalkylalkyl; and
$R^3$ is phenyl optionally substituted by one or more substituents selected from the group consisting of halo, $C_1$-$C_6$trihaloalkyl and $C_1$-$C_6$trihaloalkoxy.

11. The method of claim 10, wherein the compound is {4-[6-(2-Cyclopropyl-ethoxy)-pyridazin-3-yl]-piperazin-1-yl}-(2-trifluoromethyl-phenyl)-methanone.

12. The method of claim 1, wherein:
x and y are each 1;
W is —S(O)$_t$— (where t is 0, 1 or 2);
V is —C(O)— or —C(S)—;
$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;
$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;
$R^4$ and $R^5$ are each hydrogen; and
$R^6$, $R^{6a}$, $R^7$, $R^{7a}$, $R^8$, $R^{8a}$, $R^9$ and $R^{9a}$ are each hydrogen.

13. The method of claim 12, wherein:
V is —C(O)—;
$R^2$ is $C_7$-$C_{12}$aralkyl optionally substituted by one or more substituents selected from halo, cyano, nitro, hydroxy, $C_1$-$C_6$alkyl, $C_1$-$C_6$trihaloalkyl or $C_1$-$C_6$trihaloalkoxy;
$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N(R$^{12}$)$_2$, —OC(O)R$^{12}$, —C(O)OR$^{12}$, —S(O)$_2$N(R$^{12}$)$_2$, cycloalkyl, heterocyclyl, heteroaryl and heteroarylcycloalkyl; and
each $R^{12}$ is independently selected from hydrogen, $C_1$-$C_6$alkyl, $C_3$-$C_6$cycloalkyl, aryl or aralkyl.

14. The method of claim 13, wherein:
$R^2$ is $C_7$-$C_{12}$aralkyl optionally substituted by one or more substituents selected from halo, $C_1$-$C_6$alkyl, $C_1$-$C_6$trihaloalkyl or $C_1$-$C_6$trihaloalkoxy; and
$R^3$ is phenyl optionally substituted by one or more substituents selected from the group consisting of halo, $C_1$-$C_6$trihaloalkyl and $C_1$-$C_6$trihaloalkoxy.

15. The method of claim 14, wherein the compound is selected from the group consisting of the following:
[4-(6-Phenethylsulfanyl-pyridazin-3-yl)-piperazin-1-yl]-(2-trifluoromethyl-phenyl)-methanone;
{4-[6-(2-Phenyl-ethanesulfinyl)-pyridazin-3-yl]-piperazin-1-yl}-(2-trifluoromethyl-phenyl)-methanone; and {4-[6-(2-Phenyl-ethanesulfonyl)-pyridazin-3-yl]-piperazin-1-yl}-(2-trifluoromethyl-phenyl)-methanone.

16. The method of claim 12, wherein:

V is —C(O)—;

$R^2$ is $C_1$-$C_{12}$alkyl or $C_2$-$C_{12}$alkenyl;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

17. The method of claim 16, wherein $R^3$ is phenyl optionally substituted by one or more substituents selected from the group consisting of halo, $C_1$-$C_6$trihaloalkyl and $C_1$-$C_6$trihaloalkoxy.

18. The method of claim 17, wherein the compound is {-4-[6-(3-Methyl-butylsulfanyl)-pyridazin-3-yl]-piperazin-1-yl}-(2-trifluoromethyl-phenyl)-methanone.

19. The method of claim 1, wherein:

x and y are each 1;

W is —N($R^1$)—;

V is —C(O)— or —C(S)—;

$R^1$ is hydrogen or $C_1$-$C_6$alkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

$R^4$ and $R^5$ are each hydrogen; and $R^6$, $R^{6a}$, $R^7$, $R^{7a}$, $R^8$, $R^{8a}$, $R^9$ and $R^{9a}$ are each hydrogen.

20. The method of claim 19, wherein:

V is —C(O)—;

$R^1$ is hydrogen or $C_1$-$C_6$alkyl;

$R^2$ is $C_7$-$C_{12}$aralkyl optionally substituted by one or more substituents selected from halo, cyano, nitro, hydroxy, $C_1$-$C_6$alkyl, $C_1$-$C_6$trihaloalkyl or $C_1$-$C_6$trihaloalkoxy;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

21. The method of claim 20, wherein $R^3$ is phenyl optionally substituted by one or more substituents selected from the group consisting of halo, $C_1$-$C_6$trihaloalkyl and $C_1$-$C_6$trihaloalkoxy.

22. The method of claim 21, wherein the compound is selected from the group consisting of the following:

[4-(6-Phenethylamino-pyridazin-3-yl)-piperazin-1-yl]-(2-trifluoromethyl-phenyl)-methanone; and {4-[6-(Methyl-phenethyl-amino)-pyridazin-3-yl]-piperazin-1-yl}-(2-trifluoromethyl-phenyl)-methanone.

23. The method of claim 19, wherein:

V is —C(O)—;

$R^1$ is hydrogen or $C_1$-$C_6$alkyl;

$R^2$ is $C_1$-$C_{12}$alkyl, $C_2$-$C_{12}$alkenyl, $C_3$-$C_{12}$cycloalkyl or $C_4$-$C_{12}$cycloalkylalkyl;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

24. The method of claim 1, wherein:

x and y are each 1;

W is —N($R^1$)S(O)$_2$—;

V is —C(O)— or —C(S)—;

$R^1$ is hydrogen or $C_1$-$C_6$alkyl;

$R^2$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl, and $C_3$-$C_{12}$heteroarylalkyl;

$R^3$ is selected from the group consisting of $C_1$-$C_{12}$alkyl, $C_2$-$C_{12}$alkenyl, $C_2$-$C_{12}$hydroxyalkyl, $C_2$-$C_{12}$hydroxyalkenyl, $C_2$-$C_{12}$alkoxyalkyl, $C_3$-$C_{12}$cycloalkyl, $C_4$-$C_{12}$cycloalkylalkyl, aryl, $C_7$-$C_{12}$aralkyl, $C_3$-$C_{12}$heterocyclyl, $C_3$-$C_{12}$heterocyclylalkyl, $C_1$-$C_{12}$heteroaryl and $C_3$-$C_{12}$heteroarylalkyl;

$R^4$ and $R^5$ are each hydrogen; and $R^6$, $R^{6a}$, $R^7$, $R^{7a}$, $R^8$, $R^{8a}$, $R^9$ and $R^{9a}$ are each hydrogen.

25. The method of claim 24, wherein:

V is —C(O)—;

$R^1$ is hydrogen or $C_1$-$C_6$alkyl;

$R^2$ is $C_1$-$C_{12}$alkyl, $C_2$-$C_{12}$alkenyl, $C_3$-$C_{12}$cycloalkyl or $C_4$-$C_{12}$cycloalkylalkyl;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N($R^{12}$)$_2$, —OC(O)$R^{12}$, —C(O)O$R^{12}$, —S(O)$_2$N($R^{12}$)$_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

26. The method of claim 25, wherein:

$R^2$ is $C_1$-$C_{12}$alkyl; and $R^3$ is phenyl optionally substituted by one or more substituents selected from the group consisting of halo, $C_1$-$C_6$trihaloalkyl and $C_1$-$C_6$trihaloalkoxy.

27. The method of claim 26, wherein the compound is Propane-1-sulfonic acid {6-[4-(2-trifluoromethyl-benzoyl)-piperazin-1-yl]-pyridazin-3-yl}-amide.

28. The method of claim 24, wherein:

V is —C(O)—;

$R^1$ is hydrogen or $C_1$-$C_6$alkyl;

$R^2$ is $C_7$-$C_{12}$aralkyl optionally substituted by one or more substituents selected from halo, cyano, nitro, hydroxy, $C_1$-$C_6$alkyl, $C_1$-$C_6$trihaloalkyl or $C_1$-$C_6$trihaloalkoxy;

$R^3$ is phenyl optionally substituted by one or more substituents selected from the group consisting of halo, cyano, nitro, hydroxy, $C_1$-$C_6$alkyl, $C_1$-$C_6$trihaloalkyl, $C_1$-$C_6$trihaloalkoxy, $C_1$-$C_6$alkylsulfonyl, —N$(R^{12})_2$, —OC(O)$R^{12}$, —C(O)O$R^{12}$, —S(O)$_2$N$(R^{12})_2$, cycloalkyl, heterocyclyl, heteroaryl and heteroarylcycloalkyl; and each $R^{12}$ is independently selected from hydrogen, $C_1$-$C_6$alkyl, $C_3$-$C_6$cycloalkyl, aryl or aralkyl.

29. The method of claim 1, wherein the mammal is a mouse.

* * * * *